(12) United States Patent
Billot et al.

US007053085B2

(10) Patent No.: US 7,053,085 B2
(45) Date of Patent: May 30, 2006

(54) EP$_4$ RECEPTOR AGONIST, COMPOSITIONS AND METHODS THEREOF

(75) Inventors: Xavier Billot, Montreal (CA); John Colucci, Kirkland (CA); Yongxin Han, Kirkland (CA); Marie-Claire Wilson, Carlsbad Springs (CA); Robert N. Young, Senneville (CA)

(73) Assignee: Merck & Co. Inc., Rahway, NJ (US)

( * ) Notice: Subject to any disclaimer, the term of this patent is extended or adjusted under 35 U.S.C. 154(b) by 142 days.

(21) Appl. No.: 10/797,257

(22) Filed: Mar. 10, 2004

(65) Prior Publication Data
US 2004/0198701 A1 Oct. 7, 2004

Related U.S. Application Data

(60) Provisional application No. 60/457,700, filed on Mar. 26, 2003.

(51) Int. Cl.
*C07D 265/06* (2006.01)
*C07D 265/32* (2006.01)
*A61K 31/5355* (2006.01)
*A61K 31/535* (2006.01)
*A61P 27/06* (2006.01)

(52) U.S. Cl. .................. 514/228.8; 544/96; 544/97; 544/44; 544/59; 546/243; 514/227.2; 514/227.5; 514/227.8; 514/315; 514/317

(58) Field of Classification Search ............. 544/96, 544/97; 514/228.8
See application file for complete search history.

(56) References Cited

U.S. PATENT DOCUMENTS

| 4,690,931 A | 9/1987 | Wick et al. |
| 5,151,444 A | 9/1992 | Ueno et al. |
| 5,296,504 A | 3/1994 | Stjernschantz et al. |
| 5,352,708 A | 10/1994 | Woodward et al. |
| 5,422,368 A | 6/1995 | Stjernschantz et al. |
| 5,889,052 A | 3/1999 | Klimko et al. |
| 6,043,275 A | 3/2000 | Maruyama et al. |
| 6,344,477 B1 | 2/2002 | Sharif |
| 6,747,037 B1 | 6/2004 | Old et al. |
| 2002/0065308 A1 | 5/2002 | Cameron et al. |

FOREIGN PATENT DOCUMENTS

| EP | 0 008 186 A1 | 7/1979 |
| EP | 0855389 B1 | 1/1998 |
| EP | 1114816 A1 | 7/2001 |
| GB | 1 524 818 | 11/1974 |
| WO | WO 94/13275 A1 | 6/1994 |
| WO | WO 00/21542 A1 | 4/2000 |
| WO | WO 01/46140 A1 | 6/2001 |
| WO | WO 01/70702 A1 | 9/2001 |
| WO | WO 02/24647 A1 | 3/2002 |
| WO | WO 02/42268 A2 | 5/2002 |
| WO | WO 02/060863 A1 | 8/2002 |
| WO | WO 01/72268 A2 | 10/2002 |
| WO | WO 02/077168 A2 | 10/2002 |
| WO | WO 03/047417 A2 | 6/2003 |
| WO | WO 03/047513 A2 | 6/2003 |
| WO | WO 03/105724 | 12/2003 |
| WO | WO 03/105847 A1 | 12/2003 |
| WO | WO 03/105868 A1 | 12/2003 |
| WO | WO 04/063158 A1 | 7/2004 |

OTHER PUBLICATIONS

P. Barraclough et al., "Heterocyclic Prostaglanding Analoughes. Part 4, Piperazine-2,5-diones, Pyrazolidine-3,5-diones, 1,2,4-Triazolidinediones, 1,3,4-Oxadiiazolidinediones and 1,3,4-Thiadiazolidinediones", 1980, pp. 2096-2105, J.C.S. Perkin I.

R. A. Schumer et al., "The Nerve of Glaucoma", 1994, pp. 37-44, vol. 112, Arch Ophthalmol.

M. Weinreb et al., "Different Pattern of Alkaline Phosphatase, Osteopontin, and Osteocalcin Expression in Developing Rate Bone Visualized by in Situ Hybridization", 1990, vol. 5, No. 8, J. of Bone and Mineral Research.

D. A. Dartt et al., "Localization of Nerves Adjacent to Goblet Cells in Rat Conjunctiva" 1994, pp. 993-1000, vol. 14, Curr. Eye Res.

L. Dandona et al., "Selective Effects of Experimental Glaucoma on Axonal Transport by Retinal Ganglion Cells to the Dorsal Lateral Geniculate Nucleus", 1991, pp. 1593-1599, vol. 32, No. 5, Investigative Ophthalmology & Visual Sciences.

E. M. Ross, "Mechanisms of Drug Action and the Realtionship Between Drug Concentration and Effect", pp. 29-41, chapter 2, Goodman and Gilman's Pharmacological Basis of Therapeutics.

I. K. Gipson et al., "Mucin Genes Expressed by the Ocular Surface Epithelium", 1997, pp. 81-98, vol. 16, No. 1, Progress in Retinal and Eye Research.

D. M. Shinar et al., "Expression of alpha V and Beta$_3$ Integrin Subunits in Rat Osteoclasts in Situ", 1993, pp. 403-413, vol. 8, No. 4, J. of Bone and Mineral Research.

M. A. Lemp et al., "Report of the National Eye Instittue/Industry Workshop on Clinical Trials in Dry Eyes", 1995, pp. 221-232. vol. 21, No. 4, CLAO Journal.

(Continued)

*Primary Examiner*—Mark L. Berch
*Assistant Examiner*—Kahsay Habte
(74) *Attorney, Agent, or Firm*—Sylvia A. Ayler; Valerie J. Camara

(57) ABSTRACT

This invention relates to potent selective agonists of the EP$_4$ subtype of prostaglandin E2 receptors, their use or a formulation thereof in the treatment of glaucoma and other conditions, which are related to elevated intraocular pressure in the eye of a patient. This invention further relates to the use of the compounds of this invention for mediating the bone modeling and remodeling processes of the osteoblasts and osteoclasts.

10 Claims, No Drawings

OTHER PUBLICATIONS

M. Abramovitz et al., "The Utilization of Recombinant Prostanoid Receptors to Determine the Affinities and Selectivities of Prostaglandins and Related Analogs", 2000, pp. 285-293, vol. 1483, Biochimica et Biophysica Acta.

P. Chomczynski et al., "Single-Step Mehtod of RNA Isolation by Acid Guanidinium Thiocyanante-Phenol-Chloroform Extraction", 1987, pp. 156-159, vol. 162, Analytical Biochemistry.

S.B. Rodan et al., "Growth Stimulation of Rat Calvaria Osteoblastic Cells by Acidic Fibroblast Growth Factor", 1987, pp. 1917-1923, vol. 121, No. 6, Endocrinology.

M. Abramovitz et al., "Human Prostanoid Receptors: Cloning and Characterization", 1995, pp. 499-504, vol. 23, Advances in Prostaglandin Thromboxane, and Leukotriene Research.

J. E. Larco et al., "Epithelioid and Fibroblastic Rat Kidney Cell Clones: Epidermal Growth Factor (EGF) Receptors and the Effect of Mouse Sarcoma Virus Transformation", 1978, pp. 335-342, vol. 94, J. Cell Physiol.

T. J. Hodgkinson et al., "Practical Asymmetric Synthesis of Both Enantiomers of 6-(Hydroxymethyl) piperidin-2-one", pp. 1141-1144, Synthesis (1998).

EP4 RECEPTOR AGONIST, COMPOSITIONS AND METHODS THEREOF

This application claims the benefit of U.S. Provisional Application Ser. No. 60/457,700, filed Mar. 26, 2003.

BACKGROUND OF THE INVENTION

Glaucoma is a degenerative disease of the eye wherein the intraocular pressure is too high to permit normal eye function. As a result, damage may occur to the optic nerve head and result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by the majority of ophthalmologists to represent merely the earliest phase in the onset of glaucoma.

Many of the drugs formerly used to treat glaucoma proved unsatisfactory. Current methods of treating glaucoma include using therapeutic agents such as pilocarpine, carbonic anhydrase inhibitors, beta-blockers, prostaglandins and the like. However, these therapies often produce undesirable local effects. As can be seen, there are several current therapies for treating glaucoma and elevated intraocular pressure, but the efficacy and the side effect profiles of these agents are not ideal. Therefore, there still exists the need for new and effective therapies with little or no side effects.

A variety of disorders in humans and other mammals involve or are associated with abnormal or excessive bone loss. Such disorders include, but are not limited to, osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in postmenopausal women. Prostaglandins such as the $PGE_2$ series are known to stimulate bone formation and increase bone mass in mammals, including man. It is believed that the four different receptor subtypes, designated $EP_1$, $EP_2$, $EP_3$, and $EP_4$ are involved in mediating the bone modeling and remodeling processes of the osteoblasts and osteoclasts. The major prostaglandin receptor in bone is $EP_4$, which is believed to provide its effect by signaling via cyclic AMP. In the present invention it is found that the formula I agonists of the $EP_4$ subtype receptor are useful for stimulating bone formation. WO 02/24647, WO 02/42268, EP 1114816, WO 01/46140 and WO 01/72268 disclose $EP_4$ agonists. However, they do not disclose the compounds of the instant invention.

SUMMARY OF THE INVENTION

This invention relates to agonists of the $EP_4$ subtype of prostaglandin E2 receptors and their use or a formulation thereof in the treatment of glaucoma and other conditions that are related to elevated intraocular pressure in the eye of a patient. In particular, this invention relates to a series of 1,6-disubstituted piperidin-2-one, 3,4-disubstituted 1,3-oxazinan-2-one, 3,4-disubstituted 1,3-thiazinan-2-one, and 4,5-disubstituted morpholin-3-one derivatives and their use to treat ocular diseases and to provide a neuroprotective effect to the eye of mammalian species, particularly humans. This invention further relates to the use of the compounds of this invention for mediating the bone modeling and remodeling processes of the osteoblasts and osteoclasts.

More particularly, this invention relates to novel EP4 agonist having the structural formula I:

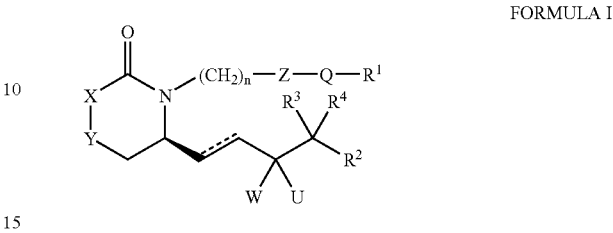

FORMULA I or a pharmaceutically acceptable salt, enantiomer, diastereomer, prodrug or mixture thereof, wherein, Q is $(CH_2)_m$, $(CH_2)_m C_{6-10}$aryl, $(CH_2)_m C_{5-10}$ heterocyclyl, $(CH_2)_m C_{3-10}$ heterocycloalkyl, $(CH_2)_m C_{3-8}$ cycloalkyl, $C(halo)_2$ said cycloalkyl, heterocycloalkyl, aryl or heterocyclyl unsubstituted or substituted with 1–3 groups of $R^a$;

X and Y independently represent $CH_2$, O, $NR^9$ or S, provided however, that X and Y are not O, $NR^9$ or S at the same time;

U represents H, C1–3 alkyl or is not present when W is =O;

W represents OH or =O, provided that U is not present when W is =O;

$R^1$ represents $(CH_2)_p$hydroxy, $(CH_2)_p$CN, $(CH_2)_p CO_2 R^{10}$, $(CH_2)_n SO_3 R^6$, $-(CH_2)_p CF_2 SO_2 NH_2$, $-(CH_2)_p SO_2 NH_2$, $-(CH_2)_p CONHSO_2 R_2$, $-(CH_2)_p SO_2 NHCOR^2$, $-(CH_2)_p PO(OH)_2$, $(CH_2)_p CONHPO_2 R^6$, $(CH_2)_p CONHR^8$, $(CH_2)_p C_{1-4}$alkoxy, $-(CH_2)_p$cycloalkyl, $(CH_2)_p$-hydroxymethylketone or $(CH_2)_n$heterocyclyl, said heterocyclyl unsubstituted or substituted with 1 to 3 groups of $R^a$ and optionally containing an acidic hydroxyl group;

$R^2$ independently represents $C_{1-10}$ alkyl, $(CH_2)_m C_{6-10}$aryl, $(CH_2)_m C_{5-10}$heterocyclyl, $(CH_2)_m C_{3-10}$ heterocycloalkyl, $(CH_2)_m C_{3-8}$ cycloalkyl, $O-C_{1-10}$alkyl, $O-C_{6-10}$aryl, $O-C_{3-10}$cycloalkyl, $O-C_{3-10}$ heterocycloalkyl, $O-C_{3-10}$ heterocycloalkyl, provided that when $R^2$ is $O-C_{1-10}$alkyl, $O-C_{6-10}$aryl, $O-C_{3-10}$cycloalkyl, $O-C_{3-10}$ heterocycloalkyl, or $O-C_{3-10}$ heterocycloalkyl, $R^3$ and $R^4$ are not halogen, said alkyl, cycloalkyl, heterocycloalkyl, aryl or heterocyclyl unsubstituted or substituted with 1–3 groups of $R^a$;

$R^3$ and $R^4$ independently represents hydrogen, halogen, or $C_{1-6}$ alkyl, or $R^3$ and $R^4$ may be taken together to form a 3–7 membered carbon ring optionally interrupted with 1–2 heteroatoms chosen from O, S, SO, $SO_2$, and $NR^9$;

$R^6$ and $R^7$ independently represents hydrogen, or $C_{1-4}$ alkyl;

$R^8$ represents hydrogen, acyl, or sulfonyl;

$R^9$ represents hydrogen, $C_{1-6}$ alkyl, said alkyl optionally substituted with 1–3 halogen, CN, OH, $C_{1-6}$ alkoxy, $C_{1-6}$ acyloxy or amino;

$R^{10}$ represents hydrogen, $C_{1-10}$ alkyl, $C_{3-10}$ cyclcoalkyl, $(CH_2)_p C_{6-10}$ aryl, $(CH_2)_p C_{5-10}$ heterocyclyl, $CR^6 R^7 OC(O)O$ $C_{3-10}$ cycloalkyl or $CR^6 R^7 OC(O)O$ $C_{1-10}$ alkyl;

Z represents a triple bond, O, S, $(C(R^b)_2)_n$, or Ch=CH;

$R^b$ represents hydrogen, C1–6 alkyl or halogen;

$R^a$ represents $C_{1-6}$ alkoxy, $C_{1-6}$ alkyl, $CF_3$, nitro, amino, cyano, $C_{1-6}$ alkylamino, halogen, or Ra further represents for aryls and heterocyclyl, $SC_{1-6}$alkyl, $SC_{6-10}$aryl, $SC_{5-10}$ heterocyclyl, $CO_2R^6$, $OC_{6-10}$aryl, $OC_{5-10}$heterocyclyl, $CH_2OC_{1-6}$ alkyl, $CH_2SC_{1-6}$ alkyl, $CH_2O$aryl, $CH_2S$aryl;

----- represents a double or single bonds;
p represents 0–3;
n represents 0–4; and
m represents 0–8.

This and other aspects of the invention will be realized upon inspection of the invention as a whole.

DETAILED DESCRIPTION OF THE INVENTION

The invention is described herein in detail using the terms defined below unless otherwise specified.

The term "therapeutically effective amount", as used herein, means that amount of the $EP_4$ receptor subtype agonist of formula I, or other actives of the present invention, that will elicit the desired therapeutic effect or response or provide the desired benefit when administered in accordance with the desired treatment regimen. A preferred therapeutically effective amount relating to the treatment of abnormal bone resorption is a bone formation, stimulating amount. Likewise, a preferred therapeutically effective amount relating to the treatment of ocular hypertension or glaucoma is an amount effective for reducing intraocular pressure and/or treating ocular hypertension and/or glaucoma.

"Pharmaceutically acceptable" as used herein, means generally suitable for administration to a mammal, including humans, from a toxicity or safety standpoint.

The term "prodrug" refers to compounds which are drug precursors which, following administration and absorption, release the claimed drug in vivo via some metabolic process. A non-limiting example of a prodrug of the compounds of this invention would be an acid of the pyrrolidinone group, where the acid functionality has a structure that makes it easily hydrolyzed after administration to a patient. Exemplary prodrugs include acetic acid derivatives that are non-narcotic, analgesics/non-steroidal, anti-inflammatory drugs having a free $CH_2COOH$ group (which can optionally be in the form of a pharmaceutically acceptable salt, e.g. —$CH_2COO$–Na+), typically attached to a ring system, preferably to an aromatic or heteroaromatic ring system.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When the alkyl group is said to be substituted with an alkyl group, this is used interchangeably with "branched alkyl group".

Cycloalkyl is a species of alkyl containing from 3 to 15 carbon atoms, without alternating or resonating double bonds between carbon atoms. It may contain from 1 to 4 rings, which are fused. Examples of cycloalkyl groups are cyclopropyl, cyclobutyl, cyclopentyl, cyclohexyl, and cycloheptyl.

Alkoxy refers to $C_1$–$C_6$ alkyl-O-, with the alkyl group optionally substituted as described herein. Examples of alkoxy groups are methoxy, ethoxy, propoxy, butoxy and isomeric groups thereof.

Halogen (halo) refers to chlorine, fluorine, iodine or bromine.

Aryl refers to aromatic rings e.g., phenyl, substituted phenyl and the like, as well as rings which are fused, e.g., naphthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined. Preferred substituted aryls include phenyl and naphthyl.

The term "heterocycloalkyl" refers to a cycloalkyl group (nonaromatic) having 3 to 10 carbon atoms in which one of the carbon atoms in the ring is replaced by a heteroatom selected from O, S or N, and in which up to three additional carbon atoms may be replaced by hetero atoms.

The term "cycloalkyl" refers to a cyclic alkyl group (nonaromatic) having 3 to 10 carbon atoms.

The term "heteroatom" means O, S or N, selected on an independent basis.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one or two additional carbon atoms is optionally replaced by a heteroatom selected from O or S, and in which from 1 to 3 additional carbon atoms are optionally replaced by nitrogen heteroatoms, said heteroaryl group being optionally substituted as described herein. Examples of this type are pyrrole, pyridine, oxazole, thiazole, tetrazole, and oxazine. For purposes of this invention the tetrazole includes all tautomeric forms. Additional nitrogen atoms may be present together with the first nitrogen and oxygen or sulfur, giving, e.g., thiadiazole.

The term heterocyclyl or heterocyclic, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom, which results in the creation of a stable structure. A fused heterocyclic ring system may include carbocyclic rings and need include only one heterocyclic ring. The term heterocycle or heterocyclic includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, tetrazolyl, thiamorpholinyl, thiamorpholinyl sulfoxide, thiazolyl, thiazolinyl, thienofuryl, thienothienyl, thienyl, and triazolyl.

For purposes of this invention, heterocyclyls containing acidic hydroxyl groups are those heterocyclyl groups that have an acidic hydroxy atom and can have a pKa in the range of 3 to 7. Non-limiting examples of heterocyclyls containing acidic hydroxyl groups are:

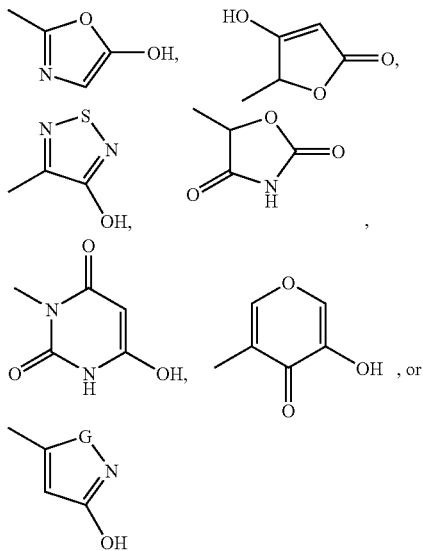

G is —C(R$^c$)$_3$,

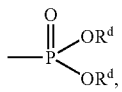

—N(R$^e$)$_2$, O, or S and each R$^c$ independently is H, fluorine, cyano or C$_{1-4}$ alkyl;

each R$^d$ independently is H, C$_{1-4}$ alkyl, or a pharmaceutically acceptable cation;

each R$^e$ independently is H, —C(=O)—R$^f$, or —SO$_2$R$^e$, wherein R$^f$ is C$_{1-4}$ linear alkyl or phenyl The term "agonist" as used herein means EP$_4$ subtype compounds of formula I interact with the EP4 receptor to produce maximal, super maximal or submaximal effects compared to the natural agonist, PGE2. See Goodman and Gilman, The Pharmacological Basis of Therapeutics, 9th edition, 1996, chapter 2.

One embodiment of this invention is realized when R$^1$ is (CH$_2$)$_p$CN, (CH$_2$)$_p$CO$_2$R$^{10}$, —(CH$_2$)$_p$PO(OH)$_2$, (CH$_2$)$_p$CONHPO$_2$R$^6$, (CH$_2$)$_p$CONHR$^8$, or (CH$_2$)$_n$heterocyclyl, said heterocyclyl unsubstituted or substituted with 1 to 3 groups of R$^a$ and all other variables are as originally described. A subembodiment of this invention is realized when Z is a (C(R$^b$)$_2$)$_n$. Another subembodiment of this invention is when Z is Sulfur. When R$^1$ is (CH$_2$)$_p$CO$_2$R$^{10}$, and Z is sulfur, the sulfur is hexavalent. Another embodiment of this invention is when Z is O.

Another embodiment of this invention is realized when R$^1$ is (CH$_2$)$_p$CO$_2$R$^{10}$ and all other variables are as originally described. A subembodiment of this invention is realized when X and Y are CH$_2$, Z is (C(R$^b$)$_2$)$_n$, Q is (CH$_2$)$_m$, R$^3$ and R$^4$ are halogen and all other variables are as originally described.

Another embodiment of this invention is realized when R$^1$ is (CH$_2$)$_m$C$_{5-10}$heterocyclyl, said heterocyclyl unsubstituted or substituted with 1 to 3 groups of R$^a$ and all other variables are as originally described. A subembodiment of this invention is realized when Z is a (C(R$^b$)$_2$)$_n$. Another subembodiment of this invention is realized when Z is S. Another embodiment of this invention is when Z is O.

Another embodiment of this invention is realized when R$^2$ is (CH$_2$)$_m$C$_{6-10}$aryl, said aryl unsubstituted or substituted with 1 to 3 groups of R$^a$ and all other variables are as originally described.

A sub-embodiment of this invention is realized when R$^1$ is (CH$_2$)$_p$CO$_2$R$^{10}$, —(CH$_2$)$_p$PO(OH)$_2$, (CH$_2$)$_p$CONHPO$_2$R$^6$, (CH$_2$)$_p$CONHR$^8$, or (CH$_2$)$_p$-tetrazolyl said tetrazolyl unsubstituted or substituted with a R$_a$ group and all other variables are as originally described. A subembodiment of this invention is realized when Z is a (C(R$^b$)$_2$)$_n$. Another subembodiment of this invention is realized when Z is S. Another embodiment of this invention is when Z is O.

Still another embodiment of this invention is realized when R$^2$ is a phenyl unsubstituted or substituted with 1 to 3 groups of R$^a$ and all other variables are as originally described.

Yet another embodiment of this invention is realized when R$^1$ is (CH$_2$)$_p$-tetrazolyl and R$^2$ is phenyl, said tetrazolyl unsubstituted or substituted with an R$^a$ group and phenyl is unsubstituted or substituted with 1–3 groups of R$^a$, and all other variables are as originally described. A subembodiment of this invention is realized when Z is a (C(R$^b$)$_2$)$_n$. Another subembodiment of this invention is realized when Z is S. Another embodiment of this invention is when Z is O.

Still another embodiment of this invention is realized when U is H and W is OH.

Still another embodiment of this invention is realized when U is C1–3 alkyl and W is OH.

Still another embodiment of this invention is realized when Q represents (CH$_2$)$_n$, or C(halo)$_2$ and all other variables are as originally described. A subembodiment of this invention is realized when Z is a (C(R$^b$)$_2$)$_n$. Another subembodiment is realized when Z is S. Still another subembodiment is realized when Z is O Still another embodiment of this invention is realized when Y represents CH$_2$, X is O, S or CH$_2$, W is OH, U is H or methyl, R$^3$ is H, F or CH$_2$ and R$^2$ is phenyl, thienyl, naphthyl, benzothioenyl, benzofuranyl, or biphenyl, said phenyl, thienyl, naphthyl, benzothioenyl, benzofuranyl, or biphenyl unsubstituted or substituted with 1–3 groups of R$^a$ and all other variables are as originally described.

Compounds of this invention are:

7-{(2R)-2-[(1E,3R)-4,4-difluoro-3-hydroxy-4-phenylbut-1-enyl]-6-oxopiperidin-1-yl}heptanoic acid;

7-{(4R)-4-[(1E,3R)-4,4-difluoro-3-hydroxy-4-phenylbut-1-enyl]-2-oxo-1,3-oxazinan-3-yl}heptanoic acid;

7-{(4R)-4-[(1E,3R)-4,4-difluoro-3-hydroxy-4-phenylbut-1-enyl]-2-oxo-1,3-thiazinan-3-yl}heptanoic acid;

7-{(2R)-2-[(3R)-4,4-difluoro-3-hydroxy-4-phenylbutyl]-6-oxopiperidin-1-yl}heptanoic acid;

7-{(4S)-4-[(3R)-4,4-difluoro-3-hydroxy-4-phenylbutyl]-2-oxo-1,3-oxazinan-3-yl}heptanoic acid;

7-{(4S)-4-[(3R)-4,4-difluoro-3-hydroxy-4-phenylbutyl]-2-oxo-1,3-thiazinan-3-yl}heptanoic acid;

7-{(2R)-2-[(3R)-3-hydroxy-4-phenylbutyl]-6-oxopiperidin-1-yl}heptanoic acid;

7-{(4S)-4-[(3R)-3-hydroxy-4-phenylbutyl]-2-oxo-1,3-oxazinan-3-yl}heptanoic acid;

7-{(4S)-4-[(3R)-3-hydroxy-4-phenylbutyl]-2-oxo-1,3-thiazinan-3-yl}heptanoic acid;

isopropyl 7-{(2R)-2-[(1E,3R)-4,4-difluoro-3-hydroxy-4-phenylbut-1-enyl]-6-oxopiperidin-1-yl}heptanoate;
isopropyl 7-{(4R)-4-[(1E,3R)-4,4-difluoro-3-hydroxy-4-phenylbut-1-enyl]-2-oxo-1,3oxazinan-3-yl}heptanoate;
isopropyl 7-{(4R)-4-[(1E,3R)-4,4-difluoro-3-hydroxy-4-phenylbut-1-enyl]-2-oxo-1,3-thiazinan-3-yl}heptanoate;
(6R)-6-[(1E,3R)-4,4-difluoro-3-hydroxy-4-phenylbut-1-enyl]-1-[6-(2H-tetraazol-5-yl)hexyl]piperidin-2-one;
(4R)-4-[(1E,3R)-4,4-difluoro-3-hydroxy-4-phenylbut-1-enyl]-3-[6-(2H-tetraazol-5-yl)hexyl]-1,3-oxazinan-2-one;
(4R)-4-[(1E,3R)-4,4-difluoro-3-hydroxy-4-phenylbut-1-enyl]-3-[6-(2H-terazol-5-yl)hexyl]-1,3-thiazinan-2-one;
(5S)-5-[(1E,3R)-4,4-difluoro-3-hydroxy-4-phenylbut-1-enyl]-4-[6-(2H-tetraazol-5-yl)hexyl]morpholin-3-one;
(6S)-6-[(1E,3R)-4,4-difluoro-3-hydroxy-4-phenylbut-1-enyl]-1-[6-(2H-tetraazol-5-yl)hexyl]piperazin-2-one;
(5S)-5-[(1E,3R)-4,4-difluoro-3-hydroxy-4-phenylbut-1-enyl]-4-[6-(2H-tetraazol-5-yl)hexyl]thiomorpholin-3-one;
5-(3-{(2R)-2-[(1E,3S)-3-hydroxy-4-phenylbut-1-enyl]-6-oxopiperidin-1-yl}propyl)thiophene-2-carboxylic acid;
5-(3-{(4R)-4-[(1E,3S)-3-hydroxy-4-phenylbut-1-enyl]-2-oxo-1,3-oxazinan-3-yl}propyl)thiophene-2-carboxylic acid;
5-(3-{(4R)-4-[(1E,3S)-3-hydroxy-4-phenylbut-1-enyl]-2-oxo-1,3-thiazinan-3-yl}propyl)thiophene-2-carboxylic acid;
5-(3-{(2R)-2-[(1E,3R)-4,4-difluoro-3-hydroxy-4-phenylbut-1-enyl]-6-oxopiperidin-1-yl}propyl)thiophene-2-carboxylic acid;
5-(3-{(4R)-4-[(1E,3R)-4,4-difluoro-3-hydroxy-4-phenylbut-1-enyl]-2-oxo-1,3-oxazinan-3-yl}propyl)thiophene-2-carboxylic acid;
5-(3-{(4R)-4-[(1E,3R)-4,4-difluoro-3-hydroxy-4-phenylbut-1-enyl]-2-oxo-1,3-thiazinan-3-yl}propyl)thiophene-2-carboxylic acid;
(6R)-6-[(1E,3R)-4,4-difluoro-3-hydroxy-4-phenylbut-1-enyl]-1-{3-[5-(2H-tetraazol-5-yl)thien-2-yl]propyl}piperidin-2-one;
(4R)-4-[(1E,3R)-4,4-difluoro-3-hydroxy-4-phenylbut-1-enyl]-3-{3-[5-(2H-tetraazol-5-yl)thien-2-yl]propyl}-1,3-oxazinan-2-one;
(4R)-4-[(1E,3R)-4,4-difluoro-3-hydroxy-4-phenylbut-1-enyl]-3-{3-[5-(2H-tetraazol-5-yl)thien-2-yl]propyl}-1,3-thiazinan-2-one;
(6R)-6-[(3R)-4,4-difluoro-3-hydroxy-4-phenylbutyl]-1-{3-[5-(2H-tetraazol-5-yl)thien-2-yl]propyl}piperidin-2-one;
(4S)-4-[(3R)-4,4-difluoro-3-hydroxy-4-phenylbutyl]-3-{3-[5-(2H-tetraazol-5-yl)thien-2-yl]propyl}-1,3-oxazinan-2-one;
(4S)-4-[(3R)-4,4-difluoro-3-hydroxy-4-phenylbutyl]-3-{3-[5-(2H-tetraazol-5-yl)thien-2-yl]propyl}-1,3-thiazinan-2-one;
isopropyl 5-(3-{(2R)-2-[(1E,3S)-3-hydroxy-4-phenylbut-1-enyl]-6-oxopiperidin-1-yl}propyl)thiophene-2-carboxylate;
isopropyl 5-(3-{(4R)-4-[(1E,3S)-3-hydroxy-4-phenylbut-1-enyl]-2-oxo-1,3-oxazinan-3-yl}propyl)thiophene-2-carboxylate;
isopropyl 5-(3-{(4R)-4-[(1E,3S)-3-hydroxy-4-phenylbut-1-enyl]-2-oxo-1,3-thiazinan-3-yl}propyl)thiophene-2-carboxylate;
isopropyl 5-(3-{(2R)-2-[(1E,3R)-4,4-difluoro-3-hydroxy-4-phenylbut-1-enyl]-6-oxopiperidin-1-yl}propyl)thiophene-2-carboxylate;
isopropyl 5-(3-{(4R)-4-[(1E,3R)-4,4-difluoro-3-hydroxy-4-phenylbut-1-enyl]-2-oxo-1,3-oxazinan-3-yl}propyl)thiophene-2-carboxylate;
isopropyl 5-(3-{(4R)-4-[(1E,3R)-4,4-difluoro-3-hydroxy-4-phenylbut-1-enyl]-2-oxo-1,3-thiazinan-3-yl}propyl)thiophene-2-carboxylate;
(5E)-7-{(2R)-2-[(1E,3R)-4,4-difluoro-3-hydroxy-4-phenylbut-1-enyl]-6-oxopiperidin-1-yl}hept-5-enoic acid;
(5E)-7-{(4R)-4-[(1E,3R)-4,4-difluoro-3-hydroxy-4-phenylbut-1-enyl]-2-oxo-1,3-oxazinan-3-yl}hept-5-enoic acid;
(5E)-7-{(4R)-4-[(1E,3R)-4,4-difluoro-3-hydroxy-4-phenylbut-1-enyl]-2-oxo-1,3-thiazinan-3-yl}hept-5-enoic acid;
(5E)-7-{(2R)-2-[(3R)-4,4-difluoro-3-hydroxy-4-phenylbutyl]-6-oxopiperidin-1-yl}hept-5-enoic acid;
(5E)-7-{(4S)-4-[(3R)-4,4-difluoro-3-hydroxy-4-phenylbutyl]-2-oxo-1,3-oxazinan-3-yl}hept-5-enoic acid;
(5E)-7-{(4S)-4-[(3R)-4,4-difluoro-3-hydroxy-4-phenylbutyl]-2-oxo-1,3-thiazinan-3-yl}hept-5-enoic acid;
2-(3-{(2R)-2-[(1E,3S)-3-hydroxy-4-phenylbut-1-enyl]-6-oxopiperidin-1-yl}propyl)-1,3-thiazole-5-carboxylic acid;
5-(3-{(2R)-2-[(1E,3S)-3-hydroxy-4-phenylbut-1-enyl]-6-oxopiperidin-1-yl}propyl)-1,3-thiazole-2-carboxylic acid;
5-(3-{(2R)-2-[(1E,3S)-3-hydroxy-4-phenylbut-1-enyl]-6-oxopiperidin-1-yl}propyl)-1,3-oxazole-2-carboxylic acid;
2-(3-{(2R)-2-[(1E,3R)-4,4-difluoro-3-hydroxy-4-phenylbut-1-enyl]-6-oxopiperidin-1yl}propyl)-1,3-oxazole-5-carboxylic acid;
5-(3-{(2R)-2-[(1E,3R)-4,4-difluoro-3-hydroxy-4-phenylbut-1-enyl]-6-oxopiperidin-1-yl}propyl)-1H-imidazole-2-carboxylic acid;
2-(3-{(2R)-2-[(1E,3R)-4,4-difluoro-3-hydroxy-4-phenylbut-1-enyl]-6-oxopiperidin-1-yl}propyl)-1H-imidazole-5-carboxylic acid;
2-(3-{(2R)-2-[(1E,3S)-3-hydroxy-4-phenylbut-1-enyl]-6-oxopiperidin-1yl}propyl)-1,3-oxazole-5-carboxylic acid;
5-(3-{(2R)-2-[(1E,3S)-3-hydroxy-4-phenylbut-1-enyl]-6-oxopiperidin-1yl}propyl)-1,2$\lambda^5$, 5$\lambda^5$-oxadiazole-2-carboxylic acid;
5-(3-{(2R)-2-[(1E,3S)-3-hydroxy-4-phenylbut-1-enyl]-6-oxopiperidin-1-yl}propyl)-4H-1,2,4-triazole-3-carboxylic acid;
5-((1E)-3-{(2R)-2-[(1E,3R)-4,4-difluoro-3-hydroxy-4-phenylbut-1-enyl]-6-oxopiperidin-1-yl}prop-1-enyl)thiophene-2-carboxylic acid;
5-(3-{(2R)-2-[(1E,3R)-4,4-difluoro-3-hydroxy-4-phenylbut-1-enyl]-6-oxopiperidin-1-yl}prop-1-ynyl)thiophene-2-carboxylic acid;
5-((1Z)-3-{(2R)-2-[(1E,3R)-4,4-difluoro-3-hydroxy-4-phenylbut-1-enyl]-6-oxopiperidin-1-yl}prop-1-enyl)thiophene-2-carboxylic acid;
(6R)-6-[(1E,3R)-4,4-difluoro-3-hydroxy-4-phenylbut-1-enyl]-1-{(2Z)-4-[(1H-tetraazol-5-ylmethyl)thio]but-2-enyl}piperidin-2-one;
[(4-{(2R)-2-[(1E,3R)-4,4-difluoro-3-hydroxy-4-phenylbut-1-enyl]-6-oxopiperidin-1-yl}but-2-ynyl)thio]acetic acid;
[((2Z)-4-{(2R)-2-[(1E,3R)-4,4-difluoro-3-hydroxy-4-phenylbut-1-enyl]-6-oxopiperidin-1-yl}but-2-enyl)thio]acetic acid;
[(4-{(2R)-2-[(1E,3R)-4,4-difluoro-3-hydroxy-4-phenylbut-1-enyl]-6-oxopiperidin-1-yl}butyl)thio]acetic acid;
(4-{(2R)-2-[(1E,3R)-4,4-difluoro-3-hydroxy-4-phenylbut-1-enyl]-6-oxopiperidin-1-yl}butoxy)acetic acid;

3-[(3-{(2R)-2-[(1E,3R)-4,4-difluoro-3-hydroxy-4-phenyl-but-1-enyl]-6-oxopiperidin-1-yl}propyl)thio]propanoic acid;
7-{(2R)-2-[(1E,3R)-4,4-difluoro-3-hydroxy-3-methyl-4-phenylbut-1-enyl]-6-oxopiperidin-1-yl}heptanoic acid;
7-{(2R)-2-[(1E,3S)-4,4-difluoro-3-hydroxy-3-methyl-4-phenylbut-1-enyl]-6-oxopiperidin-1-yl}heptanoic acid;
7-{(2R)-2-[(1E,3R)-4,4-difluoro-3-hydroxy-4-(2-naphthyl)but-1-enyl]-6-oxopiperidin-1-yl}heptanoic acid;
(6R)-6-[(1E,3R)-4,4-difluoro-3-hydroxy-3-methyl-4-phenylbut-1-enyl]-1-[6-(1H-tetraazol-5-yl)hexyl]piperidin-2-one;
(6R)-6-[(1E,3S)-4,4-difluoro-3-hydroxy-3-methyl-4-phenylbut-1-enyl]-1-[6-(1H-tetraazol-5-yl)hexyl]piperidin-2-one;
7-{(2R)-2-[(1E,3R)-4-(1-benzothien-2-yl)-4,4-difluoro-3-hydroxybut-1-enyl]-6-oxopiperidin-1-yl}heptanoic acid;
(6R)-6-[(3R)-4,4-difluoro-3-hydroxy-3-methyl-4-phenylbutyl]-1-[6-(1H-tetraazol-5-yl)hexyl]piperidin-2-one;
(6R)-6-[(3S)-4,4-difluoro-3-hydroxy-3-methyl-4-phenylbutyl]-1-[6-(1H-tetraazol-5-yl)hexyl]piperidin-2-one;
7-{(2R)-2-[(1E,3R)-4-(1-benzofuran-2-yl)-4,4-difluoro-3-hydroxybut-1-enyl]-6-oxopiperidin-1-yl}heptanoic acid;
7-{(2R)-2-[(1E,3R)-4-(3-chlorophenyl)-4,4-difluoro-3-hydroxybut-1-enyl]-6-oxopiperidin-1-yl}heptanoic acid;
7-{(2R)-2-[(1E,3R)-4-(3-chlorophenyl)-4,4-difluoro-3-hydroxybut-1-enyl]-6-oxopiperidin-1-yl}heptanoic acid;
7-{(2R)-2-[(1E,3R)-4,4-difluoro-3-hydroxy-4-(3-methoxyphenyl)but-1-enyl]-6-oxopiperidin-1-yl}heptanoic acid;
6-[(1E)-(3R)-3-hydroxy-4-phenyl-but-1-enyl]-1-[6-(1H-teraazol-5-yl)-hexyl]-piperidin-2-one;
7-{[(1E)-(2R)-2-(3S)-3-hydroxy-4-phenyl-but-1-enyl]-6-oxo-piperdin-1-yl}heptanoic acid;
isopropyl 7-{[(1E)-(2R)-2-(3S)-3-hydroxy-4-phenyl-but-1-enyl]-6-oxo-piperdin-1-yl}heptanoate;
isopropyl 7-{(2R)-2-[(3R)-3-hydroxy-4-phenyl-butyl]-6-oxo-piperdin-1-yl}heptanoate;
7-{[(2R)-2-(3R)-3-hydroxy-4-phenyl-butyl]-6-oxo-piperdin-1-yl}heptanoic acid;
methyl 5-{3-[(2R)-2-((1E)-(3S) 3-hydroxy-4-phenyl-but-1-enyl)-6-oxo-piperidin-1-yl]-propyl}-thiophene-2-carboxylate;
5-{3-[(2R)-2-((1E)-(3S) 3-hydroxy-4-phenyl-but-1-enyl)-6-oxo-piperidin-1-yl]-propyl}-thiophene-2-carboxylic acid;
5-{3-[(2R)-2-((3S) 3-hydroxy-4-phenyl-butyl)-6-oxo-piperidin-1-yl]-propyl}-thiophene-2-carboxylic acid;
isopropyl 5-{3-[(2R)-2-((1E)-(3S) 3-hydroxy-4-phenyl-but-1-enyl)-6-oxo-piperidin-1-yl]-propyl}-thiophene-2-carboxylate;
isopropyl 5-{3-[(2R)-2-((3S) 3-hydroxy-4-phenyl-butyl)-6-oxo-piperidin-1-yl]-propyl}-thiophene-2-carboxylate;
6-[(3R)-3-hydroxy-4-phenyl-butyl]-1-[6-(1H-teraazol-5-yl)-hexyl]-piperidin-2-one
isopropyl 7-{(2R)-2-[(1E)-4,4-difluoro-3-oxo-4-phenylbut-1-enyl]-6-oxopiperidin-1-yl}heptanoate;
7-{(2R)-2-[(3R)-4-(3-bromophenyl)-4,4-difluoro-3-hydroxybutyl]-6-oxopiperidin-1-yl}heptanoic acid;
methyl 5-{3-[(2R)-2-((1E)-(3S) 3-hydroxy-4-phenyl-but-1-enyl)-6-oxo-piperidin-1-yl]-propyl}-thiophene-2-carboxylate;
5-{3-[(2R)-2-((3S) 3-hydroxy-4-phenyl-butyl)-6-oxo-piperidin-1-yl]-propyl}-thiophene-2-carboxylic acid;
isopropyl 5-{3-[(2R)-2-((3S) 3-hydroxy-4-phenyl-butyl)-6-oxo-piperidin-1-yl]-propyl}-thiophene-2-carboxylate;
6-[(3R)-3-hydroxy-4-phenyl-butyl]-1-[6-(1H-teraazol-5-yl)-hexyl]-piperidin-2-one;
isopropyl (5Z)-7-{(2R)-2-[(1E,3R)-4,4-difluoro-3-hydroxy-4-phenylbut-1-en-1-yl]-6-oxopiperidin-1-yl}hept-5-enoate;
(5Z)-7-{(2R)-2-[(1E,3R)-4,4-difluoro-3-hydroxy-4-phenylbut-1-en-1-yl]-6-oxopiperidin-1-yl}hept-5-enoic acid;
isopropyl-7-{(4R)-4-[(1E)-4,4-difluoro-3-hydroxy-4-phenylbut-1-en-yl]-2-oxo-1,3oxanzinan-3-yl}heptanoate;
7-{(4R)-4-[(1E)-4,4-difluoro-3-hydroxy-4-phenylbut-1-en-yl]-2-oxo-1,3-oxanzinan-3-yl}heptanoic acid;

or a pharmaceutically acceptable salt, enantiomer, diastereomer, prodrug or mixture thereof.

Another embodiment of this invention is directed to a composition containing an $EP_4$ agonist of Formula I and optionally a pharmaceutically acceptable carrier.

Yet another embodiment of this invention is directed to a method for decreasing elevated intraocular pressure or treating glaucoma by administration, preferably topical or intracamaral administration, of a composition containing an $EP_4$ agonist of Formula I and optionally a pharmaceutically acceptable carrier. Use of the compounds of formula I for the manufacture of a medicament for treating elevated intraocular pressure or glaucoma or a combination thereof is also included in this invention This invention is further concerned with a process for making a pharmaceutical composition comprising a compound of formula I.

This invention is further concerned with a process for making a pharmaceutical composition comprising a compound of formula I, and a pharmaceutically acceptable carrier.

The claimed compounds bind strongly and act on $PGE_2$ receptor, particularly on the $EP_4$ subtype receptor and therefore are useful for preventing and/or treating glaucoma and ocular hypertension.

Dry eye is a common ocular surface disease afflicting millions of people. Although it appears that dry eye may result from a number of unrelated pathogenic causes, the common end result is the breakdown of the tear film, which results in dehydration of the exposed outer surface of the eye. (Lemp, Report of the Nation Eye Institute/Industry Workshop on Clinical Trials in Dry Eyes, The CLAO Journel, 21(4):221–231 (1995)). Functional EP4 receptors have been found in human conjuctival epithelial cells (see U.S. Pat. No. 6,344,477, incorporated by reference in its entirey) and it is appreciated that both human corneal epithelial cells (Progess in Retinal and Eye Research, 16:81–98(1997)) and conjuctival cells (Dartt et al. Localization of nerves adjacent to goblet cells in rat conjucntiva. Current Eye Research, 14:993– 1000 (1995)) are capable of secreting mucins. Thus, the compounds of formula I are useful for treating dry eye.

Macular edema is swelling within the retina within the critically important central visual zone at the posterior pole of the eye. It is believed that $EP_4$ agonist which lower IOP are useful for treating diseases of the macular such as macular edema or macular degeneration. Thus, another aspect of this invention is a method for treating macular edema or macular degeneration.

Glaucoma is characterized by progressive atrophy of the optic nerve and is frequently associated with elevated intraocular pressure (IOP). It is possible to treat glaucoma, however, without necessarily affecting IOP by using drugs that impart a neuroprotective effect. See Arch. Ophthalmol. Vol. 112, January 1994, pp. 37–44; Investigative Ophthamol. & Visual Science, 32, 5, Apr. 1991, pp. 1593–99. It is believed that $EP_4$ agonist which lower IOP are useful for providing a neuroprotective effect. They are also believed to be effective for increasing retinal and optic nerve head blood velocity and increasing retinal and optic nerve oxygen by lowering IOP, which when coupled together benefits optic nerve health. As a result, this invention further relates to a method for increasing retinal and optic nerve head blood velocity, or increasing retinal and optic nerve oxygen tension or providing a neuroprotective effect or a combination thereof by using an $EP_4$ agonist of formula I.

The compounds produced in the present invention are readily combined with suitable and known pharmaceutically acceptable excipients to produce compositions which may be administered to mammals, including humans, to achieve effective IOP lowering. Thus, this invention is also concerned with compositions and methods of treating ocular hypertension, glaucoma, macular edema, macular degeneration, for increasing retinal and optic nerve head blood velocity, for increasing retinal and optic nerve oxygen tension, for providing a neuroprotective effect or for a combination thereof by administering to a patient in need thereof one of the compounds of formula I alone or in combination with one or more of the following active ingredients, a β-adrenergic blocking agent such as timolol, betaxolol, levobetaxolol, carteolol, levobunolol, a parasympathomimetic agent such as pilocarpine, a sympathomimetic agents such as epinephrine, iopidine, brimonidine, clonidine, para-aminoclonidine, a carbonic anhydrase inhibitor such as dorzolamide, acetazolamide, metazolamide or brinzolamide; COSOPT®, a Maxi-K channel blocker such as Penitrem A, paspalicine, charybdotoxin, iberiotoxin, Paxicillan, Aflitram, Verroculogen, and as disclosed in WO 03/105868 (U.S. Ser. No. 60/389,205), WO 03/105724 (60/389,222), WO 03/105847 (60/458,981), 60/424,790, filed Nov. 8, 2002, 60/424,808, filed Nov. 8, 2002, Ser. No. 09/765,716, filed Jan. 17, 2001, Ser. No. 09/764,738, filed Jan. 17, 2001 and PCT publications WO 02/077168 and WO 02/02060863, all incorporated by reference in their entirety herein, and in particular Maxi-K channel blockers such as 1-(1-isobutyl-6-methoxy-1H-indazol-3-yl)-2-methylpropan-1-one; 1-[1-(2,2-dimethylpropyl)-6-methoxy-1H-indazol-3-yl]-2-methylpropan-1-one; 1-[1-(cyclohexylmethyl)-6-methoxy-1H-indazol-3-yl]-2-methylpropan-1-one; 1-(1-hexyl-6-methoxy-1H-indazol-3-yl)-2-methylpropan-1-one; 1-[1-(2-ethylhexyl)-6-methoxy-1H-indazol-3-yl]-2-methylpropan-1-one; 1-(3-isobutyryl-6-methoxy-1H-indazol-1-yl) buan-2-one; 1-(3-isobutyryl-6-methoxy-1H-indazol-1-yl)-3, 3-dimethylbutan-2-one; 1-(3-cyclopentylcarbonyl)-6-methoxy-1H-indazol-1-yl)-3,3-dimethylbutan-2-one; 1-(3, 3-dimethyl-2-oxobutyl)-6-methoxy-1H-indazole-3-carboxylic acid; and 1-[3-(3-hydroxypropanoyl)-6-methoxy-1H-indazol-1-yl]-3,3-dimethylbutan-2-one, a prostaglandin such as latanoprost, travaprost, unoprostone, rescula, S1033 (compounds set forth in U.S. Pat. Nos. 5,889,052; 5,296,504; 5,422,368; and 5,151,444); a hypotensive lipid such as lumigan and the compounds set forth in U.S. Pat. No. 5,352,708; a neuroprotectant disclosed in U.S. Pat. No. 4,690,931, particularly eliprodil and R-eliprodil as set forth in WO 94/13275, including memantine; and/or an agonist of 5-HT2 receptors as set forth in PCT/US00/31247, particularly 1-(2-aminopropyl)-3-methyl-1H-imdazol-6-ol fumarate and 2-(3-chloro-6-methoxy-indazol-1-yl)-1-methyl-ethylamine.

Use of the compounds of formula I for the manufacture of a medicament for treating ocular hypertension, glaucoma, macular edema, macular degeneration, for increasing retinal and optic nerve head blood velocity, for increasing retinal and optic nerve oxygen tension, for providing a neuroprotective effect or for a combination thereof is also included in this invention.

The $EP_4$ agonist used in the instant invention can be administered in a therapeutically effective amount intravaneously, subcutaneously, topically, transdermally, parenterally or any other method known to those skilled in the art. Ophthalmic pharmaceutical compositions are preferably adapted for topical administration to the eye in the form of solutions, suspensions, ointments, creams or as a solid insert. Ophthalmic formulations of this compound may contain from 0.001 to 5% and especially 0.001 to 0.1% of medicament. Higher dosages as, for example, up to about 10% or lower dosages can be employed provided the dose is effective in reducing intraocular pressure, treating glaucoma, increasing blood flow velocity or oxygen tension. For a single dose, from between 0.001 to 5.0 mg, preferably 0.005 to 2.0 mg, and especially 0.005 to 1.0 mg of the compound can be applied to the human eye.

The pharmaceutical preparation which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols, vegetable oils, peanut oil, polyalkylene glycols, petroleum based jelly, ethyl cellulose, ethyl oleate, carboxymethyl-cellulose, polyvinylpyrrolidone, isopropyl myristate and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000, antibacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a microparticle formulation. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates such as polyacrylic acid salts, ethylacrylates, polyactylamides; natural products such as gelatin, alginates, pectins, tragacanth, karaya, chondrus, agar, acacia; the starch derivatives such as starch acetate, hydroxymethyl starch ethers, hydroxypropyl starch, as well as other synthetic derivatives such as polyvinyl alcohol, polyvinyl pyrrolidone, polyvinyl methyl ether, polyethylene oxide, neutralized carbopol and xanthan gum, gellan gum, and mixtures of said polymer.

Suitable subjects for the administration of the formulation of the present invention include primates, man and other animals, particularly man and domesticated animals such as cats, rabbits and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The ophthalmic solution or suspension may be administered as often as necessary to maintain an acceptable IOP level in the eye. It is contemplated that administration to the mammalian eye will be from once up to three times daily.

For topical ocular administration the novel formulations of this invention may take the form of solutions, gels, ointments, suspensions or solid inserts, formulated so that a unit dosage comprises a therapeutically effective amount of the active component or some multiple thereof in the case of a combination therapy.

The compounds of the instant invention are also useful for mediating the bone modeling and remodeling processes of the osteoblasts and osteoclasts. See PCT US99/23757 filed Oct. 12, 1999 and incorporated herein by reference in its entirety. The major prostaglandin receptor in bone is $EP_4$, which is believed to provide its effect by signaling via cyclic AMP. See Ikeda T, Miyaura C, Ichikawa A, Narumiya S, Yoshiki S and Suda T 1995, In situ localization of three subtypes ($EP_1$, $EP_3$ and $EP_4$) of prostaglandin E receptors in embryonic and newborn mice., *J Bone Miner Res* 10 (sup 1):S172, which is incorporated by reference herein in its entirety. Use of the compounds of formula I for the manufacture of a medicament for mediating the bone modeling and remodeling processes are also included in this invention.

Thus, another object of the present invention is to provide methods for stimulating bone formation, i.e. osteogenesis, in a mammal comprising administering to a mammal in need thereof a therapeutically effective amount of an $EP_4$ receptor subtype agonist of formula I.

Still another object of the present invention to provide methods for stimulating bone formation in a mammal in need thereof comprising administering to said mammal a therapeutically effective amount of an $EP_4$ receptor subtype agonist of formula I and a bisphosphonate active. Use of the compounds of formula I for the manufacture of a medicament for stimulating bone formation is also included in this invention.

Yet another object of the present invention to provide pharmaceutical compositions comprising a therapeutically effective amount of an $EP_4$ receptor subtype agonist of formula I and a bisphosphonate active.

It is another object of the present invention to provide methods for treating or reducing the risk of contracting a disease state or condition related to abnormal bone resorption in a mammal in need of such treatment or prevention, comprising administering to said mammal a therapeutically effective amount of an $EP_4$ receptor subtype agonist of formula I. Use of the compounds of formula I for the manufacture of a medicament for treating or reducing the risk of contracting a disease state or condition related to abnormal bone resorption is also included in this invention.

The disease states or conditions related to abnormal bone resorption include, but are not limited to, osteoporosis, glucocorticoid induced osteoporosis, Paget's disease, abnormally increased bone turnover, periodontal disease, tooth loss, bone fractures, rheumatoid arthritis, periprosthetic osteolysis, osteogenesis imperfecta, metastatic bone disease, hypercalcemia of malignancy, and multiple myeloma.

Within the method comprising administering a therapeutically effective amount of an $EP_4$ receptor subtype agonist of formula I and a bisphosphonate active, both concurrent and sequential administration of the $EP_4$ receptor subtype agonist of formula I and the bisphosphonate active are deemed within the scope of the present invention. Generally, the formulations are prepared containing 5 or 10 mg of a bisphosphonate active, on a bisphosphonic acid active basis. With sequential administration, the agonist and the bisphosphonate can be administered in either order. In a subclass of sequential administration the agonist and bisphosphonate are typically administered within the same 24 hour period. In yet a further subclass, the agonist and bisphosphonate are typically administered within about 4 hours of each other.

A non-limiting class of bisphosphonate actives useful in the instant invention are selected from the group consisting of alendronate, cimadronate, clodronate, tiludronate, etidronate, ibandronate, neridronate, olpandronate, risedronate, piridronate, pamidronate, zolendronate, pharmaceutically acceptable salts thereof, and mixtures thereof.

A non-limiting subclass of the above-mentioned class in the instant case is selected from the group consisting of alendronate, pharmaceutically acceptable salts thereof, and mixtures thereof.

A non-limiting example of the subclass is alendronate monosodium trihydrate.

In the present invention, as it relates to bone stimulation, the agonist is typically administered for a sufficient period of time until the desired therapeutic effect is achieved. The term "until the desired therapeutic effect is achieved", as used herein, means that the therapeutic agent or agents are continuously administered, according to the dosing schedule chosen, up to the time that the clinical or medical effect sought for the disease or condition being mediated is observed by the clinician or researcher. For methods of treatment of the present invention, the compounds are continuously administered until the desired change in bone mass or structure is observed. In such instances, achieving an increase in bone mass or a replacement of abnormal bone structure with normal bone structure are the desired objectives. For methods of reducing the risk of a disease state or condition, the compounds are continuously administered for as long as necessary to prevent the undesired condition. In such instances, maintenance of bone mass density is often the objective.

Nonlimiting examples of administration periods can range from about 2 weeks to the remaining lifespan of the mammal. For humans, administration periods can range from about 2 weeks to the remaining lifespan of the human, preferably from about 2 weeks to about 20 years, more preferably from about 1 month to about 20 years, more preferably from about 6 months to about 10 years, and most preferably from about 1 year to about 10 years.

The instant compounds are also useful in combination with known agents useful for treating or preventing bone loss, bone fractures, osteoporosis, glucocorticoid induced osteoporosis, Paget's disease, abnormally increased bone turnover, periodontal disease, tooth loss, osteoarthritis, rheumatoid arthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; a cathepsin K inhibitor; an estrogen or an estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; calcitonin; Vitamin D or a synthetic Vitamin D analogue; and the pharmaceutically acceptable salts and mixtures thereof. A preferred combination is a compound of the present invention and an organic bisphosphonate. Another preferred combination is a compound of the present invention and an estrogen receptor modulator. Another preferred combination is a compound of the present invention and an estrogen. Another preferred combination is a compound of the present invention and an androgen receptor modulator. Another preferred combination is a compound of the present invention and an osteoblast anabolic agent.

Regarding treatment of abnormal bone resorption and ocular disorders, the formula I agonists generally have an $EC_{50}$ value from about 0.001 nM to about 100 microM, although agonists with activities outside this range can be useful depending upon the dosage and route of administration. In a subclass of the present invention, the agonists have an $EC_{50}$ value of from about 0.01 microM to about 10 microM. In a further subclass of the present invention, the agonists have an $EC_{50}$ value of from about 0.1 microM to about 10 microM. $EC_{50}$ is a common measure of agonist activity well known to those of ordinary skill in the art and is defined as the concentration or dose of an agonist that is needed to produce half, i.e. 50%, of the maximal effect. See also, Goodman and Gilman's, *The Pharmacologic Basis of Therapeutics*, 9th edition, 1996, chapter 2, E. M. Ross, *Pharmacodynamics, Mechanisms of Drug Action and the Relationship Between Drug Concentration and Effect*, and PCT US99/23757, filed Oct. 12, 1999, which are incoporated by reference herein in their entirety.

The herein examples illustrate but do not limit the claimed invention. Each of the claimed compounds are $EP_4$ agonists and are useful for a number of physiological ocular and bone disorders.

The compounds of this invention can be made, with some modification, in accordance with U.S. Pat. No. 6,043,275, EP0855389, WO 03/047417 (U.S. Ser. No. 60/337,228), WO 03/047513 (U.S. Ser. No. 60/338,117), U.S. Ser. No. 60/406,530 and WO 01/46140, all of which are incorporated herein by reference in their entirety. The following non-limiting schemes and examples given by way of illustration is demonstrative of the present invention.

Scheme 1

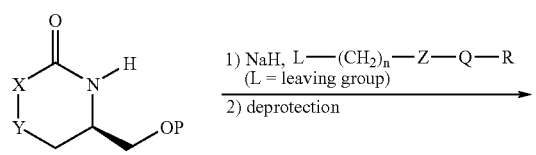

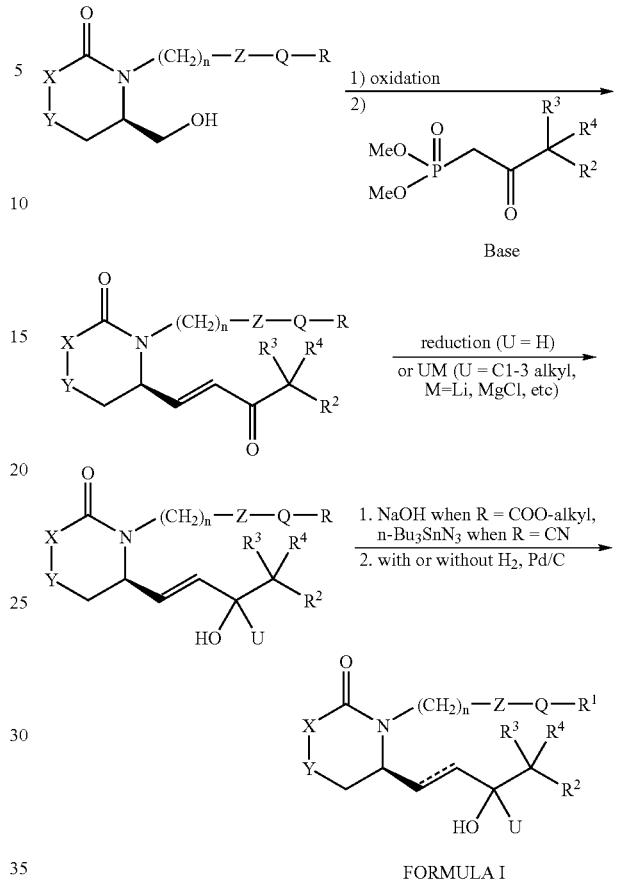

FORMULA I

PREPARATIVE EXAMPLE 1

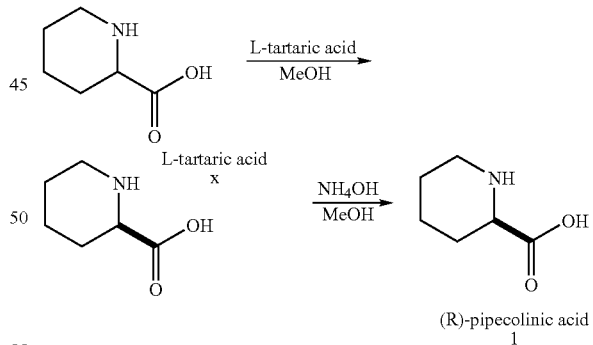

(R)-pipecolinic acid
1

To a slurry of (+/−)-pipecolinic acid (395 g, 3.06 moles) in MeOH (1.8 L) at 60° C. was added L-tartaric acid (459 g, 3.06 moles). The slurry was warmed to reflux and aged 1 h (hour). The slurry was cooled to 23° C., filtered, and the desired (R)-pipecolinic acid/L-tartaric acid filtercake was washed with MeOH (200 mL). The filtercake was air dried a white solid was isolated. The pipecolinic acid tartrate salt typically assayed at 85–89% ee.

A slurry of salt (383 g) in 2:1H$_2$O/acetone (380 mL/190 mL) was warmed to reflux (60–65° C.) until all solids had dissolved. Acetone (1330 mL) was added over 2 h while maintaining a reflux. The slurry was allowed to cool to 15–20° C. over 1 h and then filtered, washed with 4:1 acetone/H₂O (380 mL) and then air dried under vacuum. Isolated 313 g of pipecolinic acid tartrate salt (>99% ee).

To a slurry of (R)-pipecolinic acid tartrate salt (312 g) in MeOH (3.0 L) was added 28% NH₄OH (83 mL, 1.1 eq) over 0.5 h. The white slurry was aged 0.5 h at ambient temperature and then the ammonium tartrate precipitate was filtered off. The filtercake was rinsed with MeOH (300 mL). The combined filtrate and rinse was concentrated to a white solid of (1).

PREPARATIVE EXAMPLE 2

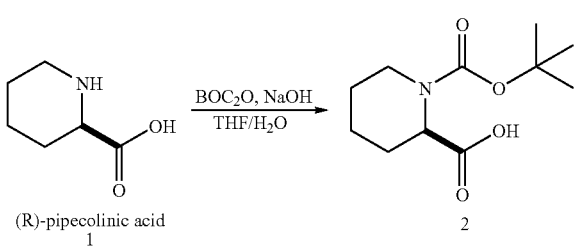

To a slurry of pipecolinic acid (109.7 g) and BOC₂O (222.4 g) in 1:1 tetrahydrofuran (THF)/H₂O (550/550 mL) was added 50% NaOH (45 mL). The slurry was warmed to reflux and aged 5 h at reflux. The solution was cooled to 23° C. and then washed with heptane (550 mL) to remove unreacted BOC₂O. The aqueous (aq.) layer was then acidified with 5N HCl (170 mL) to pH 4–5. The resulting slurry was extracted with 550 mL of tert-butyl methyl ether (MTBE). The organic layer was dried over Na₂SO₄ and then concentrated to a white solid of (2).

PREPARATIVE EXAMPLE 3

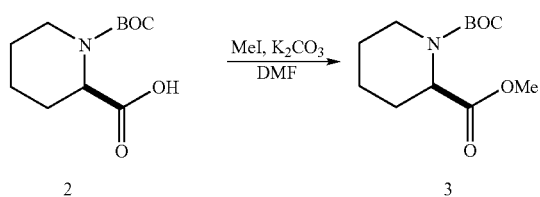

To a solution of N-BOC-pipecolinic acid (166.5 g, 726 mmoles) in 500 mL dimethylformamide (DMF) was added MeI (123.7 g, 871 mmoles) and K₂CO₃ (100.4 g, 726 moles). The reaction mixture slowly exothermed to 40° C. after 0.5 h during a 4 h age period at ambient temperature. Added MTBE (830 mL) and then washed with H₂O (2×830 mL) and 20% brine (300 mL). The organic layer was dried over Na₂SO₄ and concentrated to an oil (3).

PREPARATIVE EXAMPLE 4

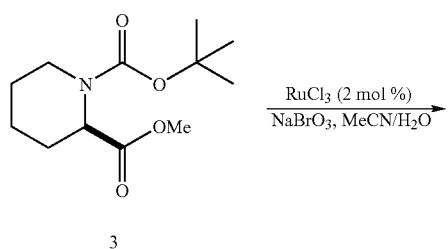

-continued

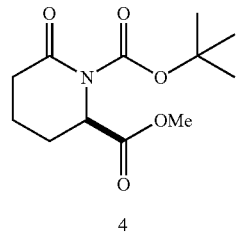

To a solution of butoxycarbonyl (Boc)-Me ester (152.6 g, 627 mmol) in MeCN (305 mL) was added RuCl₃ (2.6 g, 12.5 mmol). A solution of NaBrO₃ (142.0 g, 941 mmol) in H₂O (760 mL) was added over 2 h. The solution was aged 12 h at ambient temperature. Added EtOAc (760 mL) and cut the aqueous layer. The dark organic layer was washed with 10% Na₂SO₃ (305 mL) while the organic layer turned clear and the aqueous layer turned cloudy grey. The organic layer was washed with saturated brine (150 mL) and then dried over Na₂SO₄ to give oil (4).

PREPARATIVE EXAMPLE 5

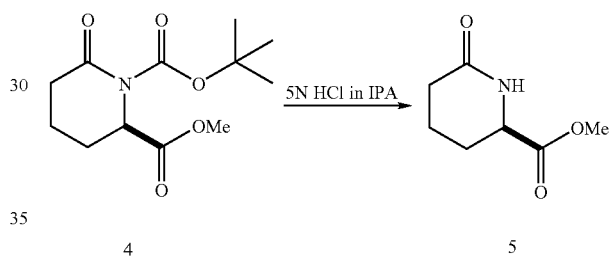

To a solution of BOC-Lactam (135.4 g, 526 mmol) in 135 mL of isopropyl alcohol (IPA) was added 5N HCl in 263 mL/1316 mmol isopropyl alcohol (IPA) over 15 min. Vigorous gas evolution occurred for 15 min and then the solution was aged 2.5 h at ambient temperature. Added EtOAc (800 mL) and washed with 15% Na₂CO₃ (350 mL). The aqueous layer was extracted with EtOAc (400 mL). The combined organic layers were dried over Na₂SO₄ and concentrated to oil (5). The enantiomeric purity was assayed at >99% ee.

PREPARATIVE EXAMPLE 6

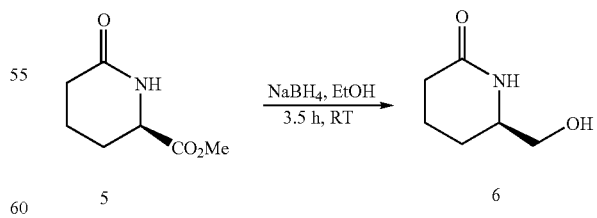

To a solution of lactam ester (8.10 g, 51.7 mmol) in anhydrous ethanol (500 mL) was added sodium borohydride (2.5 g, 1.2 eq) in 0.5 g increments over 30 minutes. The solution was stirred for 3.5 hours at room temperature. The mixture was then treated with glacial acetic acid (2.8 equiv) and the precipitate removed by filtering through a plug of celite. The filtrate was then concentrated in vacuo and the resulting oil solidified upon standing under vacuum. The crude product was dissolved in CH$_2$Cl$_2$ (50 mL), treated with KHCO$_3$ (1.5 equiv), aged for 1 h, filtered through a plug of Celite and the resulting filtrate was concentrated in vacuo to give the title compound 6, which was used directly in the next step without further purification.

PREPARATIVE EXAMPLE 7

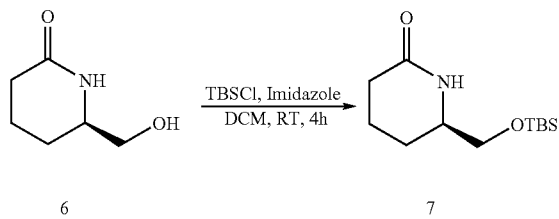

To a solution of the lactam alcohol (10 g, 77.5 mmol, 1.0 equiv) in anhydrous CH$_2$Cl$_2$ (50 mL) at 0° C. under N$_2$ atmosphere was added imidazole (6.9 g, 100.8 mmol, 1.3 equiv, (the amount of imidazole was adjusted to neutralize any AcOH from the previous step) and 14 g/93.0 mmol/1.2 equiv of tert-butyldimethylsilyl chloride (TBSCl). The resulting mixture was warmed to room temperature (RT) and aged for 4 hours. Once the reaction was judged complete, CH$_2$Cl$_2$ (100 mL) was added, followed by 1N HCl solution (30 mL). The organic layer was separated and the aqueous layer was back-extracted with CH$_2$Cl$_2$ (2×50 mL). The combined organic layer was washed with 20% NaHCO$_3$ solution (40 mL), brine, dried over MgSO$_4$, filtered and concentrated in vacuo to give the desired compound as white solid. The silicon-containing byproducts can be removed by washing the solid with cold heptane (3 mL/g) at −78° C. to give the titled compound 7.

PREPARATIVE EXAMPLE 8

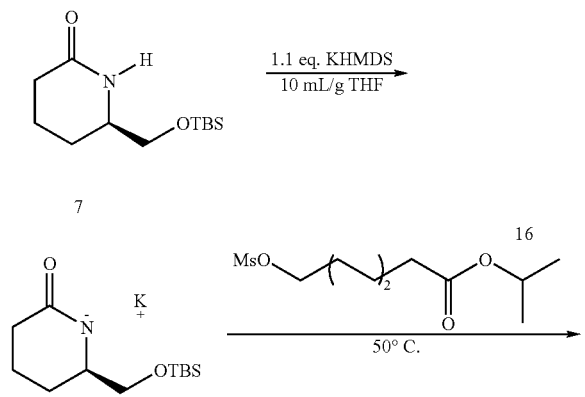

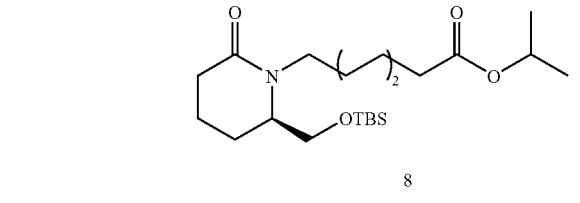

To a 15° C. solution of lactam 7 (2.0 g, 8.22 mmoles) in THF (KF<200 ppm) was added 1.90 g/9.04 mmoles of solid potassium bis[trimethylsilyl]amide (KHMDS) in 20 mL of tetrahydrofuran (THF) and aged for 10 min at room temperature (rt). Freshly prepared mesylate (0.93 g, 8.22 mmoles, KF<800 ppm) was added to the solution as a neat oil and the reaction was heated to 50° C. and aged for 2.5–3.5 h. The reaction was cooled to rt and diluted with MTBE (20 mL) and water (20 mL). The aqueous (aq.) layer was cut and the organics were washed with sat'd. brine (10 mL). Upon drying over Na$_2$SO$_4$, the solvent was removed to yield crude yellow oil 8.

PREPARATIVE EXAMPLE 9

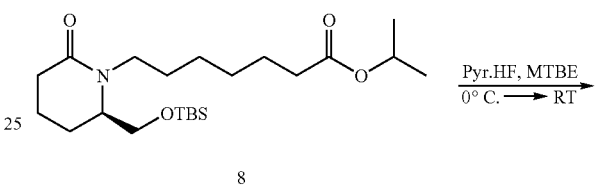

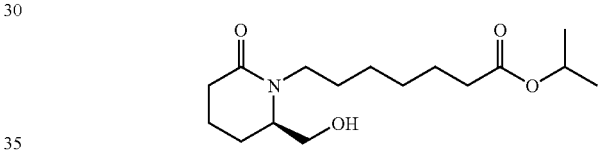

To a solution of the tert-butyldimethylsilyl (TBS)-protected lactam (10 g, 24.2 mmol, 1 equiv) in dry MTBE (40 mL) at 0° C. under N$_2$ atmosphere was added a 70% solution of HF•Pyridine (4.84 g, 169 mmol, 7 equiv) over 15 min. The resulting mixture was allowed to warm to RT and aged for 12 h, at which the reaction was judged complete by HPLC and $^1$HNMR analysis. The mixture was then diluted with MTBE (100 mL) and washed with cold H$_2$O (30 mL). The organic layer was then treated with saturated Na$_2$CO$_3$ (25 mL), brine, dried over MgSO$_4$, filtered and concentrated in vacuo. The resulting crude oil (9) is used directly in the next step. If desired, the alcohol can be purified by SiO$_2$ gel flash column chromatography (40:1 CH$_2$Cl$_2$:MeOH).

PREPARATIVE EXAMPLE 10

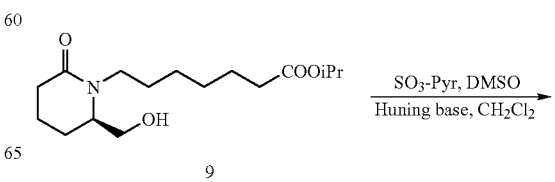

-continued

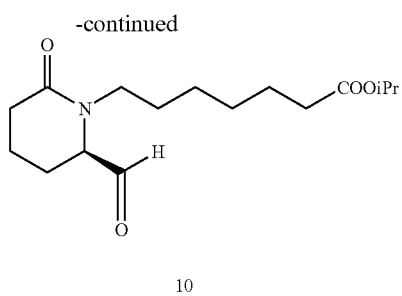

10

To a cold solution (0° C.) of alcohol 9 (9.46 g, 31.6 mmol), DMSO (237.3 mmol, 16.9 mL, 7.5 equiv), and Hunig base (16.5 mL, 94.9 mmol, 3 equiv) in dichloromethane (95 mL) was added $SO_3 \cdot$Pyridine (15 g, 94.9 mmol, 3 equiv) as a solid over 15 minutes. The resulting solution was aged at 0° C. for 1.5 h, at which complete consumption of the starting material was observed. The reaction mixture was then diluted with EtOAc (150 mL) and washed with cold 4N aqueous HCl (35 mL). The organic layer was separated and treated successively with saturated $NaHCO_3$ solution and brine. The solution then dried over $MgSO_4$ filtered and concentrated in vacuo to give the corresponding aldehyde (7.8 g, 83% assay yield), which was used in the next step without further purification.

PREPARATIVE EXAMPLE 11

Preparation of Sodium Phosphonate 14

Step 1

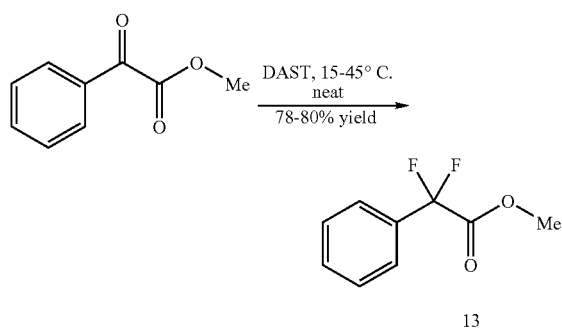

To a neat solution of methyl benzoylformate ($PhCOCO_2Me$, 25 g, 0.15 mol, 1 equiv) at 15° C. under $N_2$ atmosphere was added neat diethylaminosulfur trifluoride (DAST, 34.4 g, 0.21 mol, 1.4 equiv) at a rate such that the internal temperature was maintained below 45° C. At the end of the addition, the resulting brown solution was allowed to cool to RT and aged for 3 more hours, at which time a complete consumption of starting material was observed by high performance liquid chromatography (HPLC) and gas chromatography/mass spectroscopy (GC/MS). The reaction mixture was then poured slowly into a mixture of ice/$H_2O$ (NOTE: exothermic!) and the product was extracted with MTBE (3×). The combined organic layer was then neutralized slowly to a pH of 7 with a cold solution of 20% aqueous $Na_2CO_3$ (NOTE: gas evolution), washed with brine, dried over $MgSO_4$, filtered and concentrated in vacuo. The crude product was purified by vacuum distillation (bp=103–105° C. at 24–25 torr) to give the desired product (13) as slightly yellow oil.

Step 2

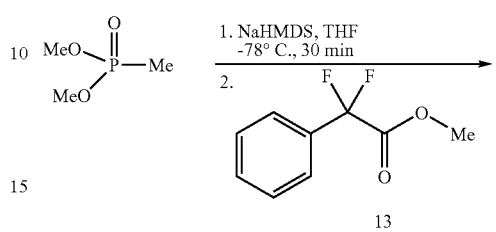

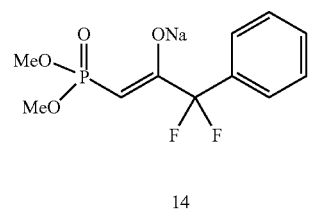

To a solution of dimethyl methylphosphonate (28 g, 0.23 mol, 1.05 equiv) in dry THF (400 mL, KF=30 ppm) under $N_2$ atm at −78° C. was slowly added a 2M solution of sodium bis(trimethylsilyl)amide in THF (115 mL, 0.23 mol, 1.05 equiv) over 15 min. The resulting solution was aged for 30 min and then treated with neat methyl difluoroester ($PhCF_2CO_2Me$, 40 g, 0.22 mol, 1.0 equiv) over 15 min. The reaction mixture was aged at −78° C. for 1 h, slowly warmed to RT and concentrated to about a quarter of its original volume and added MTBE (400 mL) over 0.5 h. The resulting suspension was further aged at RT for 0.5 h and filtered. The wet cake was washed with MTBE (100 mL) and dried in vacuo under a stream of $N_2$. The product was isolated as white solid (14).

PREPARATIVE EXAMPLE 12

Preparation of Compound 16

Step 1

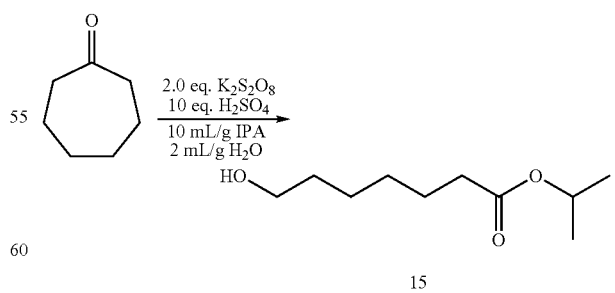

To a 10° C. solution of water (250 mL), IPA (1250 mL) and concentrated sulfuric acid (600 mL, 11.1 moles) was added solid potassium persulfate (600 g, 2.22 moles) in one portion. Cycloheptanone (131.5 mL) was diluted to 250 mL total volume with EPA and this solution was added via addition funnel to the persulfate slurry over 15 min with the temperature maintained <15° C. throughout the addition. The reaction was aged at 15° C. for 16–20 h. Once all of the cycloheptanone had reacted, the reaction was filtered to remove the salts, keeping the filtrate cold. The filtrate was diluted with MTBE (1250 mL), sat'd brine (1 L), and water (500 mL), with the temperature maintained <30° C. Upon transfer to a separatory funnel, the phases were allowed 1 h to settle and the aqueous layer was cut. The organic layer was washed with sat'd. Na$_2$CO$_3$ (2×1 L), or until the aq. cut remained basic. The solution was diluted with hexanes (1.25 L) and dried over Na$_2$SO$_4$ for 1 h. The solvent was removed under vacuum and the oil was vacuum distilled to yield pure ester (16). (bp 125° @ 4 mm Hg)

Step 2

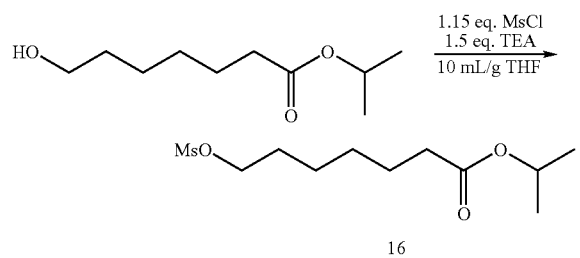

16

To a −10° C. solution of ester (10 g, 0.05 moles) and triethylamine (11.1 mL, 0.08 moles) in dry THF (100 mL) was added Methanesulfonyl chloride (MsCl-4.75 mL, 0.06 moles) (diluted 1:1 in THF) with the temperature maintained <10° C. throughout the addition. The reaction was aged for 30 min @ 0–5° C. Upon completion, the reaction was diluted with hexanes (100 mL) and quenched with water (50 mL). The aq. layer was cut and the organic layer was dried over Na$_2$SO$_4$ for 30 min. The solvent was removed under vacuum and gave a yellow oil (16). The mesylate should be prepared fresh prior to lactam alkylation in order to minimize impurities.

EXAMPLE 1 isopropyl7-{(2R)-2-[(1E)-4,4-difluoro-3-oxo-4-phenylbut-1-en-1-yl]-6-oxopiperidin-1-yl}heptanoate

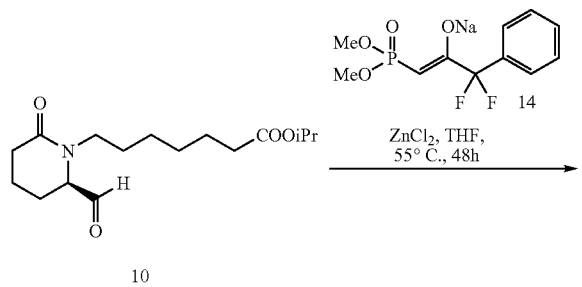

10

-continued

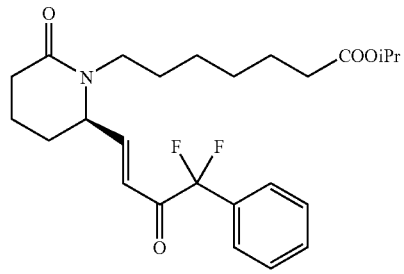

11

To a solution of sodium phosphonate 14 (13.7 g, 45.7 mmol, 1.4 equiv) in THF (130 mL) at 0° C. under nitrogen was added ZnCl$_2$ (3.33 g, 24.5 mmol, 0.75 equiv). The resulting mixture was stirred at rt for 15 minutes and then treated with a solution of aldehyde 10 (9.7 g, 32.66 mmol, 1 equiv) in THF (10 mL). The resulting suspension was then heated to 50° C. for 50 h, at which a 94–97% conversion was observed. The mixture was then concentrated to about a third of its volume, diluted with EtOAc (130 mL), washed with H$_2$O (30 mL) and brine. The organic layer was then dried over MgSO$_4$, filtered and concentrated to give yellow oil (11), which can be purified by SiO$_2$ gel flash chromatography (19:1→9:1 toluene:acetone).

EXAMPLE 2

7-{(2R)-2-[(1E,3R)-4,4-difluoro-3-hydroxy-4-phenylbut-1-en-1-yl]-6-oxopiperidin-1-yl}heptanoate
(12)

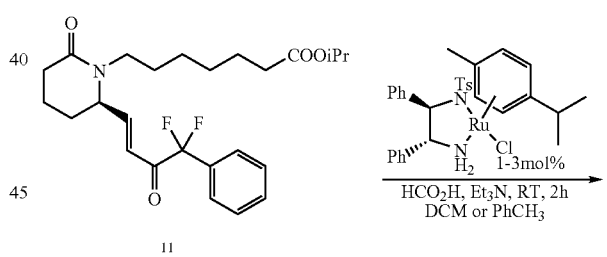

To a solution of the enone (450 mg, 1 mmol, 1.0 equiv) in 0.5 M/~4.5 mL/g anhydrous PhCH$_3$ or dichloromethane (DCM) under N$_2$ atmosphere was added Et$_3$N (0.14 mL, 1 mmol, 1.0 equiv) and HCO$_2$H (0.05 mL, 1.2 mmol, 1.2 equiv) at room temperature (RT). The resulting solution was stirred for 10 min and then treated with solid (R,R)-(−)-Ru-TsDPEN-cymene complex[1] (19 mg, 0.03 mmol, 0.03 equiv)

all at once. The reaction mixture was then aged at RT for 2 h, at which a complete consumption of starting material was observed. Tert-butyl methyl ether-MTBE (5 mL) was added followed by 1N HCl (2 mL). The organic layer was separated, washed with saturated Na₂CO₃, brine, dried over MgSO₄, filtered and concentrated in vacuo to give the final compound as viscous oil.

The catalyst can also be generated in situ by mixing 0.02 mol equiv of [RuCl₂(p-cymene)₂] and 0.04 mol equiv of the (R,R)-N-Tosyl-1,2-diphenylethylene-1,2-diamine in DCM (dichloromethane) in the presence of 0.04 mol equiv of 1M solution KOtBu in THF (tetrahydrofuran). After aging for 10 min at RT, Et₃N was added followed by HCO₂H and a solution of the enone in DCM).

The catalyst was prepared by mixing 1 mol equiv of [RuCl₂(p-cymene)₂], 2 mol equiv (R,R)-N-Tosyl-1,2-diphenylethylene-1,2-diamine and 4.2 mol equiv of Et₃N in iPrOH at 80° C. for 1 h (hour). After solvent removal, the solid was washed with cold H₂O and the recrystallized from MeOH to give the catalyst as orange solid.

EXAMPLE 3

7-{(2R)-2-[(1E, 3R)-4,4-difluoro-3-hydroxy-4-phenylbut-1-en-1-yl]-6-oxopiperidin-1-yl}heptanoic acid

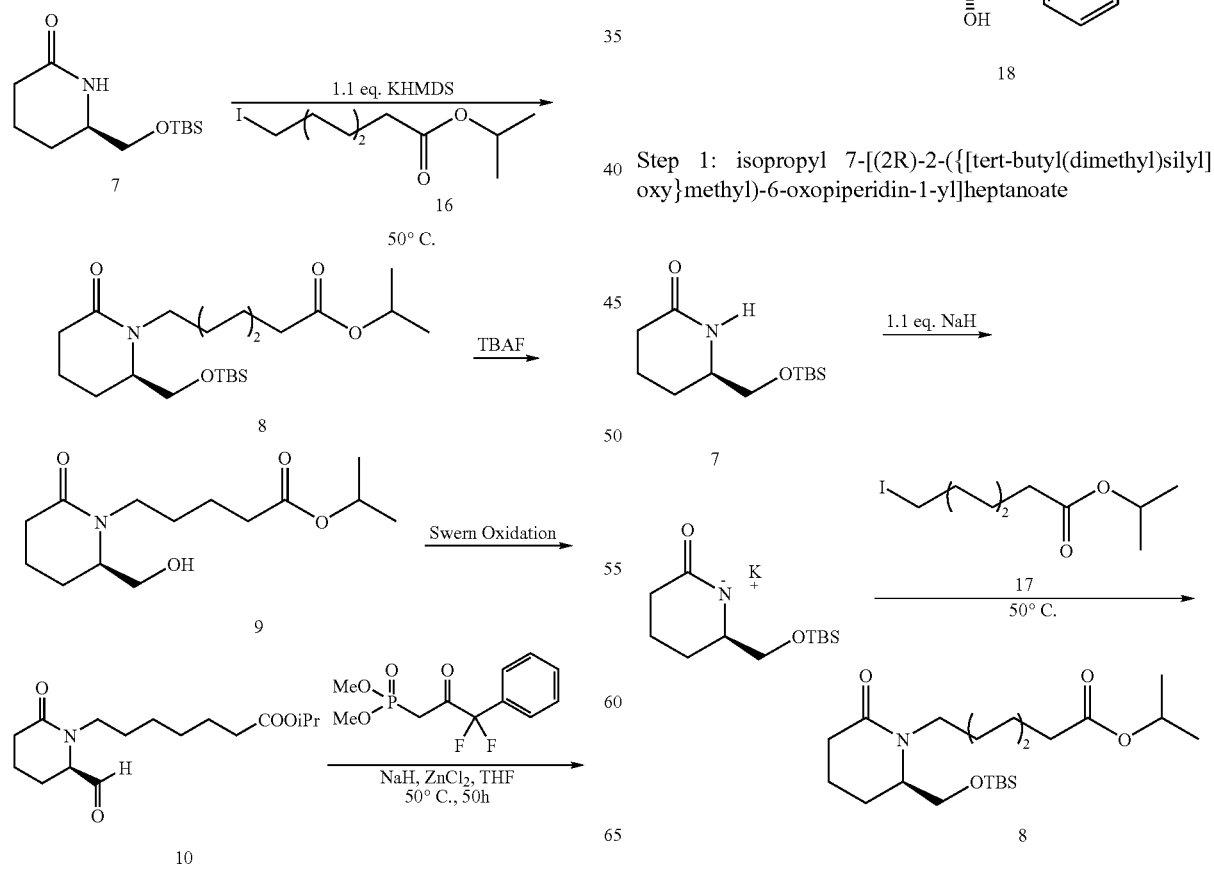

Step 1: isopropyl 7-[(2R)-2-({[tert-butyl(dimethyl)silyl]oxy}methyl)-6-oxopiperidin-1-yl]heptanoate To a solution of 7 (1.0 g, 4.1 mmol, synthesized in seven steps according to the literature procedure Synthesis 1998, 1141–1144.) in 12 mL DMF (dimethyl formamide) was added 60% sodium hydride (172 mg, 4.3 mmol) and the resulting solution was stirred for 30 min at 50° C. whereupon isopropyl-7-iodoheptanoate, 17, (1.9 g, 1.6 mL, 8.2 mmol) and tetrabutylammonium iodide (50 mg) were added. The solution was stirred at 50° C. overnight after which it was cooled to room temperature, slowly poured into saturated aqueous ammonium chloride solution and was extracted with ether. The organic phases were then combined and sequentially washed with $H_2O$, brine and dried over $Na_2SO_4$, filtered and concentrated in vacuo. The compound was purified by flash chromatography using 75–100% ethyl acetate/hexanes to yield 9 as a colorless oil. 1H NMR (500 MHz, Acetone-d6): δ 4.95 (m, 1H), 3.75 (m, 3H), 3.50 (m, 1H), 2.97 (m, 1H), 2.25 (2t, 4H), 2.00 (m, 1H), 1.93 (m, 1H), 1.82 (m, 1H), 1.70–1.56 (m, 4H), 1.52 (m, 1H), 1.40–1.28 (m, 4H), 1.22 (2s, 6H), 0.93 (s, 9H), 0.11 (s, 6H).

Step 2: isopropyl 7-[(2R)-2-(hydroxymethyl)-6-oxopiperidin-1-yl]heptanoate

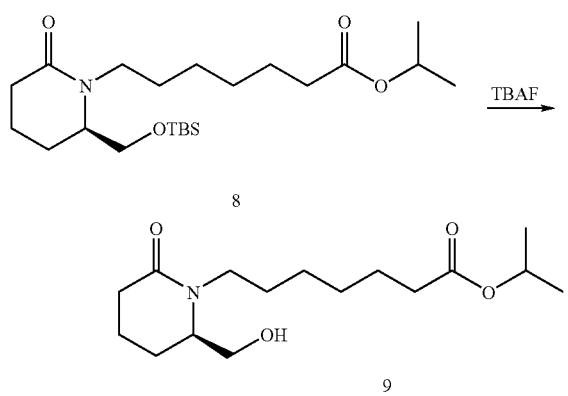

To a solution of 8 (0.80 g, 2.3 mmol) in 10 mL was added TBAF-tetrabutylammonium fluoride (0.25 mL of a 1M solution in THF) at room temperature and stirred for 18 hours. The solution was then quenched with saturated (sat'd.) $NaHCO_3$, and extracted with ethyl acetate. The organic layers were combined and washed with water then brine, dried over $MgSO_4$, filtered and concentrated in vacuo to yield 9 as a colorless oil. $^1$H NMR (500 MHz, Acetone-d6): δ 4.95 (m, 6H), 3.97 (t, 1 H, OH), 3.76 (m, 1H), 3.66 (m, 2H), 3.48 (m, 1H), 2.98 (m, 1H) 2.24 (m, 4H), 2.08 (m, 1H), 1.90 (m, 1H), 1.79 (m, 1H), 1.70–1.56 (m, 4H), 1.50 (m, 1H), 1.40–1.27 (m, 4H), 1.22 (2s, 6H).

Step 3: isopropyl 7-{(2R)-2-[(1E)-4,4-difluoro-3-oxo-4-phenylbut-1-en-1-yl]16-oxopiperidin- 1-yl}heptanoate

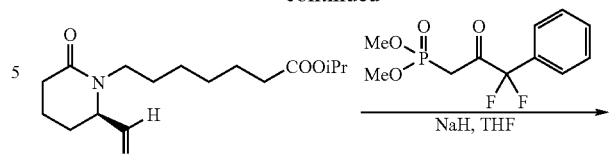

To a purged flask with $N_2$ (g) was added $CH_2Cl_2$ (40 mL) to which dimethylsulfoxide (0.115 g, 0.10 mL, 1.48 mmol) was then added. The solution was then cooled to −78° C. and during vigorous stirring oxalyl chloride (0.17 g, 0.12 mL, 1.3 mmol) was added dropwise. After 30 min a solution of 9 (0.35 g, 1.2 mmol) in 5 mL $CH_2Cl_2$ was added via cannula. Stirring was continued for another 30 min at −78° C. Triethyl amine (0.31 g, 0.43 mL, 3.1 mmol) was added dropwise and after 15 min of stirring was concentrated in vacuo without the use of the bath. A solution of 1:1 diethyl ether/ethyl acetate (100 mL) was used to filter off the triethylamine salts and the solution was concentrated in vacuo. The crude aldehyde, 10, was then diluted in 5 mL of THF and added to a solution of (2-oxo-3-phenyl-propyl)-phosphonic acid dimethyl ester (0.34 g, 1.4 mmol) and 60% sodium hydride (52 mg, 1.3 mmol) in 15 mL of THF at 0° C. which had been premixed 1 hour. Zinc chloride (x mL of a 1M solution in THF was added) and the reaction mixture was stirred overnight at 50° C. The solution was quenched with saturated aqueous ammonium chloride solution and was extracted with ethyl acetate. The organic phases were then combined, and sequentially washed with $H_2O$, brine and dried over $Na_2SO_4$, filtered and concentrated in vacuo. The compound was purified by flash chromatography using 50–80% ethyl acetate/hexanes to yield 11 as a colorless oil. 1H NMR (400 MHz, Acetone-d6): δ 7.65–7.55 (m, 5H), 7.11 (dd, 1H), 6.67 (d, 1H), 4.95 (m, 1H), 4.40 (m, 1H), 3.78 (m, 1H), 2.60 (m, 1H), 2.25 (m, 4H), 2.02 (m, 1H), 1.90 (m, 1H), 1.68 (m, 2H), 1.53–1.36 (m, 4H), 1.35–1.17 (m, 10H).

Step 4: isopropyl 7-{(2R)-2-[(1E,3R)-4,4-difluoro-3-hydroxy-4-phenylbut-1-en-1-yl]-6-oxopiperidin- 1-yl}heptanoate

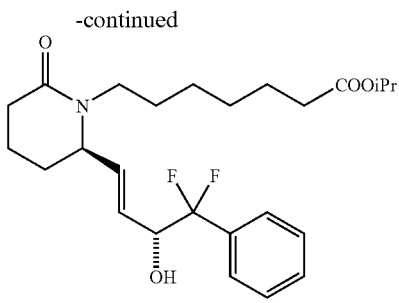

12

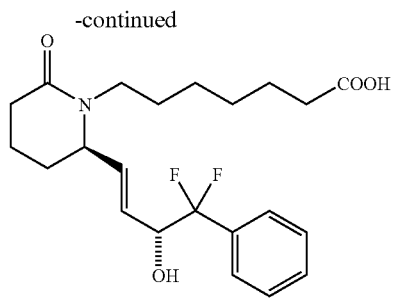

18

A. Synthesis of butyl-(S)-CBS in toluene: To a solution of (S)-CBS ligand (11.53 g, 45.5 mmol) in toluene (110 mL) was added butylboronic acid (5.1 g, 47.8 mmol) and the mixture was heated to reflux over night with a Dean stark. This final solution was 0.48 M and was used directly.

B. Reduction: To a solution of catecholborane (3.35 mL, 31.4 mmol) in toluene (400 mL) cooled to −78° C. was added 68 mL (32.6 mmol) of (S)-2-butyl-CBS oxazaborolidine solution under nitrogen and the mixture was stirred at the temperature for 1 hour (h). Ketone 11 (7 g, 15.6 mmol) in toluene (420 mL) was added dropwise in 1 h under nitrogen and the mixture stirred at the temperature until all starting material disappeared (usually in 30 min). To the mixture was then added 200 mL 1N HCl and the mixture allowed to warm to room temperature with vigorous stirring. The mixture was extracted with ethyl acetate (emulsion developed during extraction and the suspension was filtered through celite to remove emulsion). The crude product was purified by flash chromatograph. Eluting with EA/hexanes (70–100%) gave the desired alcohol as a mixture of two diastereomers in a ratio of 12:1. The mixture was easily separated by prep HPLC (high performance liquid chromatograpy) using a chiral Pak AD® column using 50% iPrOH in hexanes as eluants (monitoring at λ 214 nm). The undesired isomer came out first followed by the desired isomer 12.

$^1$H NMR (400 MHz, Acetone-$d_6$): δ 7.6–7.5 (m, 2H), 7.5–7.4 (m, 3H), 5.80 (dd, 1H), 5.6 (dd, 1H), 5.0–4.9 (m, 2H), 4.7–4.6 (m, 1H), 4.1–4.0 (m, 1H), 3.8–3.7 (m, 1H), 2.6–2.5 (m,1H), 2.3–2.2 (m, 4H), 1.9–1.8 (m, 1H), 1.75–1.55 (m, 5H), 1.55–1.4 (m, 2H), 1.4–1.22 (m, 4H), 1.22 (d, 6H).

Step 5: 7-{(2R)-2-[(1E, 3R)-4,4-difluoro-3-hydroxy-4-phenylbut-1-en-1-yl]-6-oxopiperidin-1-yl} heptanoic acid

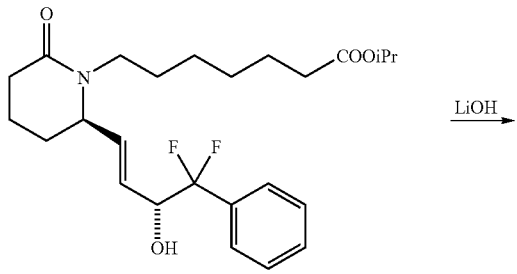

12

To a solution of 12 (39 mg, 0.089 mmol) in 2.75 mL 2.5:2.5:1 THF:MeOH:water, at 0° C., was added lithium hydroxide (145 µL of a 2M solution in water) and the resulting solution was allowed to warm to room temperature and stirred overnight. To the solution was added a 1M aqueous solution of HCl (1 mL) and the solution was extracted with ethyl acetate. The organic phases were then combined, washed with brine, dried over $MgSO_4$, filtered and concentrated in vacuo. The compound was purified by flash chromatography using 49–45%/1–5%/1 drop $CH_2Cl_2$/methanol/acetic acid to yield 18 as a colorless oil. $^1$H NMR (500 MHz, Acetone-d6): δ 7.6–7.5 (m, 5H), 5.8 (dd, 1H), 5.6 (dd, 1H), 5.6 (bs, 1H), 4.6 (m, 1H), 4.1 (m, 1H), 3.7 (m, 1H), 2.6 (m, 1H), 2.4–2.2 (m, 4H), 1.9–1.2 (m, 12H).

The following Examples 4 through 13 can be made in accordance with Examples 1–3 with the appropriate modifications.

EXAMPLE 4

7-{(2R)-2-[(3R)-4-(3-bromophenyl)-4,4-difluoro-3-hydroxybutyl]-6-oxopiperidin-1-yl}heptanoic acid MS (+ESI): m/z 490.1 (M+1)$^+$.

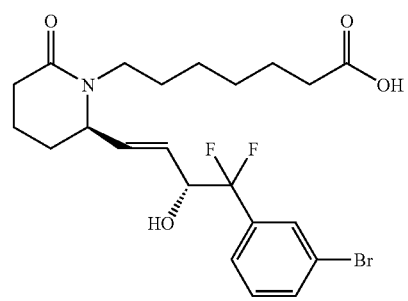

19

EXAMPLE 5

7-{[(2R)-2-(3R)-3-hydroxy-4-phenyl-butyl]-6-oxo-piperdin-1-yl}heptanoic acid $^1$H NMR (400 MHz, $CD_3OD$): δ 7.3–7.1 (m, 5H), 3.8–3.7 (m, 2H), 3.4 (m, 1H), 2.9–2.7(m, 3H), 2.3 (m, 4H), 1.9–1.3 (m, 16H); MS (−ESI): m/z 374.2 (M−1)$^-$.

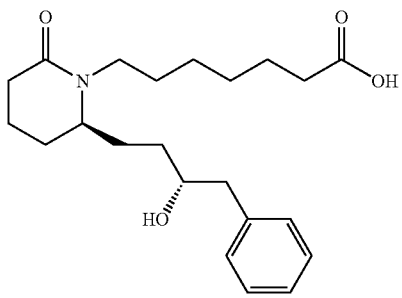

EXAMPLE 6 methyl 5-{3-[(2R)-2-((1E)-(3S) 3-hydroxy-4-phenyl-but-1-enyl)-6-oxo-piperidin-1-yl]-propyl}-thiophene-2-carboxylate $^1$H NMR (400 MHz, CDCl$_3$): δ 7.6 (d, 1H), 7.2–7.1 (m, 5H), 6.7 (d, 1H), 5.5 (m, 2H), 4.3 (m, 1H), 3.8–3.7 (m, 2H), 3.8 (s, 3H), 2.8–2.6 (m, 6H), 2.3–2.2 (m, 2H), 1.9–1.2 (m, 6H).

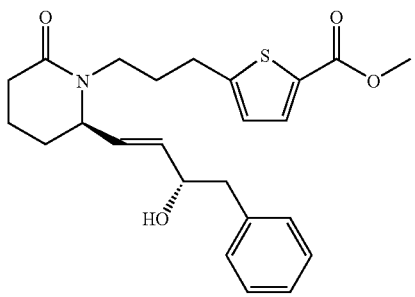

EXAMPLE 7

5-{3-[(2R)-2-((1E)-(3S) 3-hydroxy-4-phenyl-but-1-enyl)-6-oxo-piperidin-1-yl]-propyl}-thiophene-2-carboxylic acid $^1$H NMR (400 MHz, CD$_3$OD): δ 7.6 (d, 1H), 7.2–7.1 (m, 5H), 6.9 (d, 1H), 5.5 (m, 2H), 4.3 (m, 1H), 3.9 (m, 1H), 3.7 (m, 1H), 2.9–2.6 (m, 5H), 2.2 (m, 2H), 1.9–1.5 (m, 6H); MS (−ESI): m/z 412.1 (M−1)$^-$.

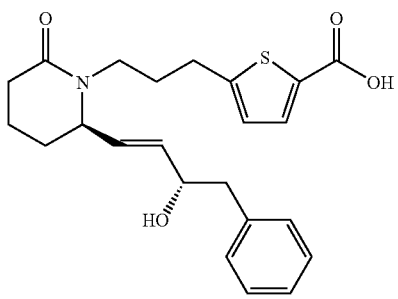

EXAMPLE 8

5-{3-[(2R)-2-((3S) 3-hydroxy-4-phenyl-butyl)-6-oxo-piperidin-1-yl]-propyl}-thiophene-2-carboxylic acid $^1$H NMR (400 MHz, CD$_3$OD): δ 7.6 (d, 1H), 7.3–7.1 (m, 5H), 6.9 (d, 1H), 1H), 3.0–2.9 (m, 1H), 2.8–2.5 (m, 4H), 2.3 (m, 2H), 2.0–1.3 (m, 10H); MS (−ESI): m/z 414.1 (M−1)$^-$.

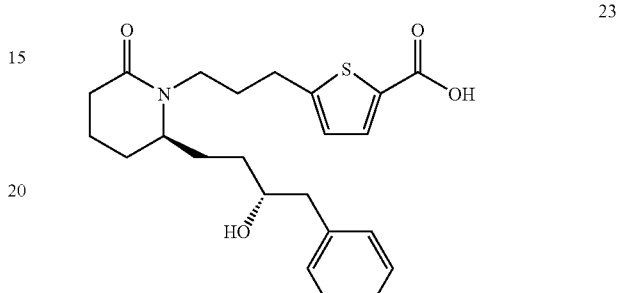

EXAMPLE 9 isopropyl 5-{3-[(2R)-2-((1E)-(3S) 3-hydroxy-4-phenyl-but-1-enyl)-6-oxo-piperidin-1-yl]-propyl}-thiophene-2-carboxylate $^1$H NMR (400 MHz, CDCl$_3$): δ 7.6 (d, 1H), 7.3–7.1 (m, 5H), 6.8 (d, 1H), 5.5 (m, 2H), 5.1 (m, 1H), 4.4 (m, 1H), 3.9–3.8 (m, 2H), 3.3 (br s, 1H), 2.8 (m, 4H), 2.7 (m, 1H), 2.3 (m, 2H), 1.9–1.6 (m, 6H), 1.3 (dd, 6H); MS (+ESI): m/z 456.4 (M+1)$^+$.

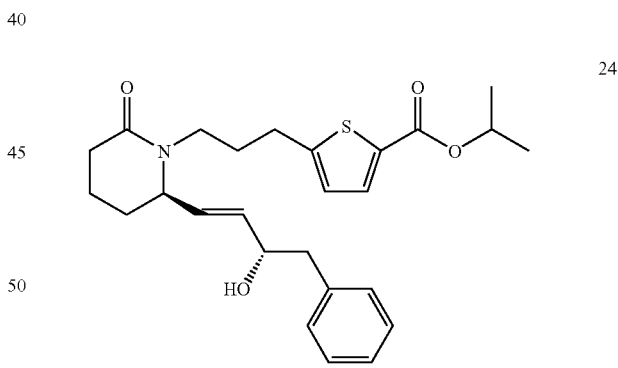

EXAMPLE 10 isopropyl 5-{3-[(2R)-2-((3S) 3-hydroxy-4-phenyl-butyl)-6-oxo-piperidin-1-yl]-propyl}-thiophene-2-carboxylate $^1$H NMR (400 MHz, CDCl$_3$): δ 7.6 (d, 1H), 7.3–7.1 (m, 5H), 6.8 (d, 1H), 5.2 (m, 1H), 3.9–3.8 (m, 2H), 3.3 (m, 1H), 2.9–2.8 (m, 4H), 2.7–2.6 (m, 1H), 2.4–2.3 (m, 3H), 2.0–1.2 (m, 10H), 1.3 (d, 6H); MS (+ESI): m/z 458.2 (M+1)$^+$.

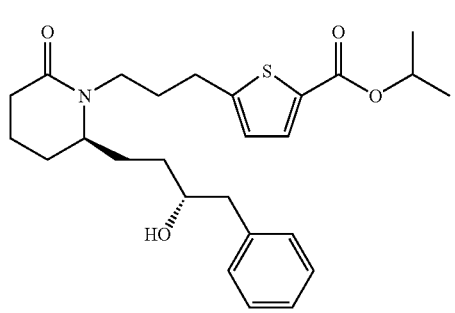

EXAMPLE 11

6-[(3R)-3-hydroxy-4-phenyl-butyl]-1-[6-(1H-teraa-zol-5-yl)-hexyl]-piperidin-2-one $^1$H NMR (400 MHz, CD$_3$OD): δ 7.3–7.1 (m, 5H), 3.8–3.7 (m, 2H), 3.3 (m, 1H), 2.9–2.7 (m, 5H), 2.3 (m, 2H), 1.9–1.3 (m, 16H); MS (+ESI): m/z 400.3 (M+1)$^+$.

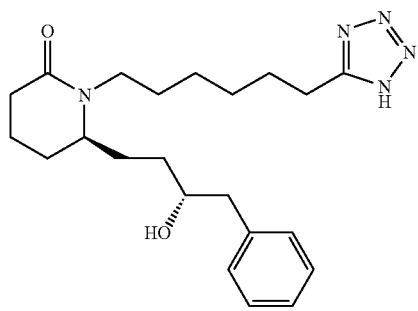

EXAMPLE 12 isopropyl (5Z)-7-{(2R)-2-[(1E,3R)-4,4-difluoro-3-hydroxy-4-phenylbut-1-en-1-yl]-6-oxopiperidin-1-yl}hept-5-enoate MS (+ESI): m/z 450.3 (M+1)$^+$.

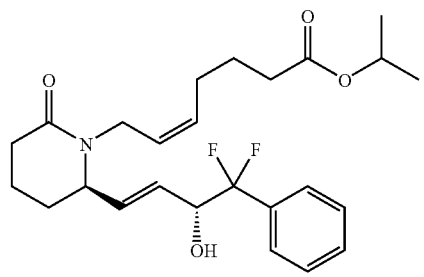

EXAMPLE 13

(5Z)-7-{(2R)-2-[(1E,3R)-4,4-difluoro-3-hydroxy-4-phenylbut-1-en-1-yl]-6-oxopiperidin-1-yl}hept-5-enoic acid MS (–ESI): m/z 406.1 (M–1)$^-$.

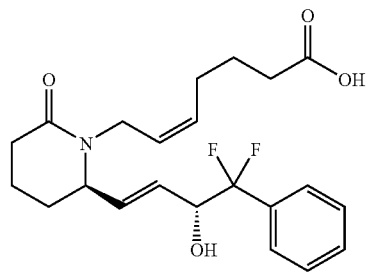

EXAMPLE 14 isopropyl-7-{(4R)-4-[(1E)-4,4-difluoro-3-hydroxy-4-phenylbut-1-en-yl]-2-oxo-1,3-oxanzinan-3-yl}heptanoate MS (+ESI): m/z 454 (M+1)$^+$.

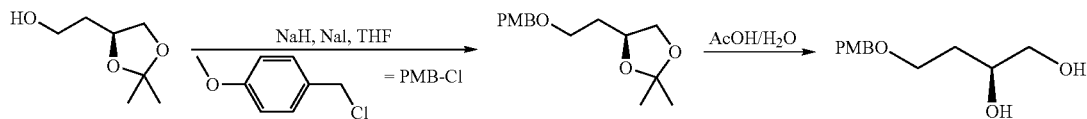

Scheme 3

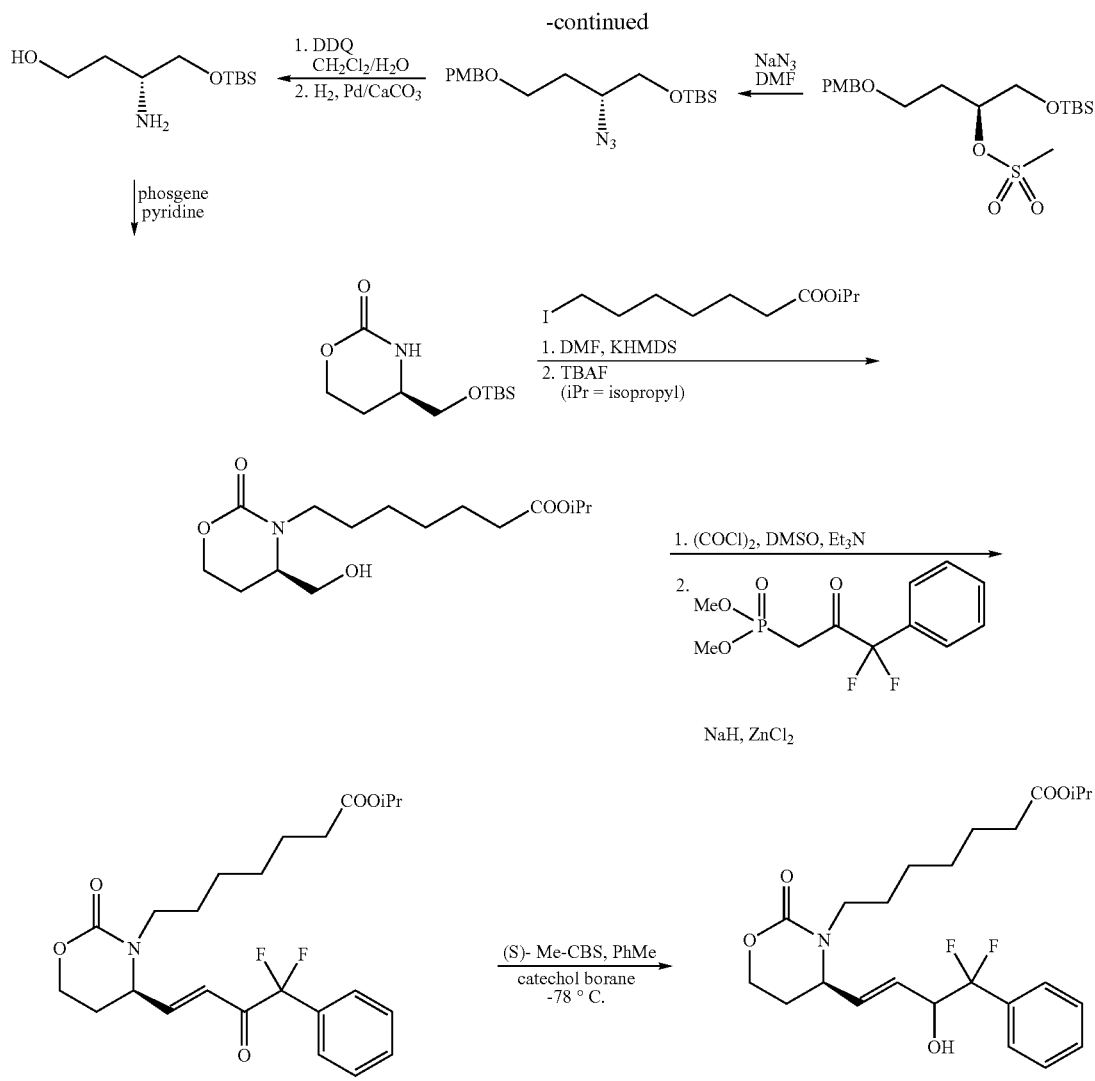

Step 1

Preparation of (4S)-4-[2-(4-methoxyphenoxy)ethyl]-2,2-dimethyl-1,3-dioxolane

To a solution of 2-[(4S)-2,2-dimethyl-1,3-dioxolan-4-yl]ethanol (Aldrich, 5 g, 34.2 mmol) in THF was added sodium hydride 60% (1.504 g, 37.6 mmol, 1.1 eq) portionwise and the mixture stirred for 1 h (cloudy solution). The mixture was cooled to 0° C. and to it was added 4-methoxybenzyl chloride (5.89 g, 37.6 mmol, 1.1 equivalent (eq.)) in one portion and the mixture stirred at the temperature for 30 min and heated to 65–70° C. overnight. After cooling to rt and quenching with saturated $NH_4Cl$/water, the mixture was extracted with ethyl acetate (2×) and the organic extracts were washed with water, brine and dried over $MgSO_4$. The mixture was filtered and the filtrate was concentrated in vacuo. The crude product was purified by silica gel chromatography (15% ethyl acetate/hexanes) to give desired product as a colorless oil. $^1$H NMR (400 MHz, Acetone-$d_6$): δ7.28 (2 H, d), 6.93–6.91 (2 H, m), 4.43 (2 H, s), 4.20–4.14 (1 H, m), 4.04–3.98 (1 H, m), 3.80 (3H, s), 3.56–3.50 (3H, m), 1.88–1.76 (2H, m), 1.31 (3H, s), 1.28 (3 H, s).

Step 2

Preparation of (2S)-4-(4-methoxyphenoxy)butane-1,2-diol

A solution of (4S)-4-[2-(4-methoxyphenoxy)ethyl]-2,2-dimethyl-1,3-dioxolane (8.2 g, 30.8 mmol) in AcOH/water was stirred at rt for 5 h and concentrated in vacuo. The residue was co-evaporated with toluene (3×) and then pumped under high vacuum to give the desired product. $^1$H NMR (400 MHz, Acetone-$d_6$): δ7.28 (2 H, d), 6.91 (2 H, d), 4.43 (2 H, s), 3.80 (3 H, s), 3.77 (1H, m), 3.66–3.42 (5 H, m), 1.86–1.76 (1 H, m), 1.68–1.60 (1 H, m).

Step 3

Preparation of (1S)-1-({[tert-butyl(dimethyl)silyl]oxy}methyl)-3-(4-methoxyphenoxy)propyl methanesulfonate To a solution of (2S)-4-(4-methoxyphenoxy)butane-1,2-diol (7 g, 30.9 mmol) and imidazole (4.21 g) in DMF (50 mL) was added t-Butyldimethylsilyl chloride (4.88 g, 32.4 mmol, 1.05 eq) in one portion at 0° C. and the mixture was stirred at the temperature for 1 h and diluted with water/ether. The layers were separated and the aqueous layer extracted with ether (2×). The extracts were combined, wased with water, brine, dried and filtered. The filtrated was concentrated in vacuo to give 10.8 g crude product (2S)-1-{[tert-butyl(dimethyl)silyl]oxy}-4-(4-methoxyphenoxy)butan-2-ol as a colorless oil. The crude NMR indicated that the product was over 95% pure and thus it was used directly without purification. $^1$H NMR (400 MHz, Acetone-$d_6$): δ7.28 (2 H, d), 6.92–6.90 (2 H, m), 4.43 (2 H, s), 3.80 (3 H, s), 3.75 (1H, m), 3.67–3.51 (5 H, m), 1.89–1.81 (1 H, m), 1.66–1.58 (1 H, m), 0.91 (s, 9H), 0.09 (s, 6 H).

To a solution of (2S)-1-{[tert-butyl(dimethyl)silyl]oxy}-4-(4-methoxyphenoxy)butan-2-ol (10.5 g, 30.8 mmol) in dichloromethane (DCM) (50 mL) at 0° C. was added triethylamine (6.5 mL) followed by MsCl (2.9 mL) dropwise and the mixture (light yellow suspension) was stirred for 1 h and quenched with water. The layers were separated and the organic layer dried over MgSO$_4$. The mixture was filtered and the filtrate was concentrated in vacuo to give the desired methanesulfonate. $^1$H NMR (400 MHz, Acetone-$d_6$): δ7.29 (2 H, d), 6.91 (2 H, d), 4.84–4.78 (1 H, m), 4.49–4.41 (2 H, m), 3.90 (1 H, dd), 3.84 (1H, dd), 3.80 (3H, s), 3.62–3.54 (2H, m), 3.09 (3 H, s), 2.04–1.90 (2 H, m), 0.91 (s, 9H), 0.12–0.06 (6 H, m).

Step 4

Preparation of {[(2R)-2-azido-4-(4-methoxyphenoxy)butyl]oxy}(tert-butyl)dimethylsilane A mixture of (1S)-1-({[tert-butyl(dimethyl)silyl]oxy}methyl)-3-(4-methoxyphenoxy)propyl methanesulfonate (13 g) and NaN$_3$ (10 g) in DMF (50 mL) was heated to 60–70° C. under N$_2$ o/n and cooled to rt. The mixture was diluted with ether/water and extracted with ether (3×). The ether extracts were washed with water, brine and then worked up as usual. The crude was purified by flash chromatography (5% ethyl acetate/hexanes) to give the desired azido product. $^1$H NMR (400 MHz, Acetone-$d_6$): δ7.29 (2 H, d), 6.92 (2 H, d), 4.45 (2 H, s), 3.87 (1 H, dd), 3.80 (3 H, s), 3.70–3.54 (4 H, m), 1.85–1.77 (1 H, m), 1.68–1.60 (1 H, m), 0.93 (9 H, s), 0.11 (6 H, s).

Step 5

Preparation of (3R)-3-amino-4-{[tert-butyl(dimethyl)silyl]oxy}butan-1-ol

To a solution of {[(2R)-2-azido-4-(4-methoxyphenoxy)butyl]oxy}(tert-butyl)dimethylsilane (4.7 g, 12.86 mmol) in 19:1 DCM/water at 0° C. was added DDQ (2,3-Dichloro-5,6-dicyano-1,4-benzoquinone) (3.5 g, 15.43 mmol, 1.2 eq) and the mixture was stirred (from 0° C. to rt) until all starting material disappeared as indicated by TLC (thin layer chromatography) analysis. Most DCM was then removed in vacuo and the residue was dissolved in ethyl acetate. The ethyl acetate solution was washed with water and saturated NaHCO$_3$ repeatedly until a pale yellow organic solution was obtained. The organic solution was dried and the crude was purified by silica gel chromatography (5% acetone/toluene) to give the desired product (3R)-3-azido-4-{[tert-butyl(dimethyl)silyl]oxy}butan-1-ol. $^1$H NMR (400 MHz, Acetone-$d_6$): δ3.89 (1 H, dd), 3.73–3.65 (5 H, m), 1.76–1.68 (1 H, m), 1.62–1.54 (1 H, m), 0.94 (9 H, s), 0.13 (6 H, s).

A mixture of (3R)-3-azido-4-{[tert-butyl(dimethyl)silyl]oxy}butan-1-ol (2.94 g) and Lindlar's catalyst (5% Pd/CaCO$_3$, 1.27 g) in ethanol (50 mL) was hydrogenated under 51 psi H$_2$ for 3.5 h and filtered. The filtrate was concentrated to give 2.97 g crude product (3R)-3-amino-4-{[tert-butyl(dimethyl)silyl]oxy}butan-1-ol with good purity. $^1$H NMR (CDCl$_3$, 400 MHz): 3.85 (2 H, t), 3.54 (1 H, dd), 3.42 (1 H, dd), 3.03–2.97 (1 H, m), 2.44 (3 H, br s), 1.64–1.52 (2 H, m), 0.92 (9 H, s), 0.08 (6 H, s).

Step 6

Preparation of (4R)-4-({[tert-butyl(dimethyl)silyl]oxy}methyl)-1,3-oxazinan-2-one To a solution of (3R)-3-amino-4-{[tert-butyl(dimethyl)silyl]oxy}butan-1-ol (2.63 g, 12 mmol) in DCM (100 mL) at 0° C. was added pyridine (3 mL) followed by phosgene (20% solution in toluene, 1.9 M, 8.5 mL) dropwise and the mixture was stirred for 30 min and allowed to warm to rt, and quenched with water. The layers were separated and the water layer extracted with DCM once. The organic layers were dried over MgSO$_4$, filtered and concentrated. The desired product (4R)-4-({[tert-butyl(dimethyl)silyl]oxy}methyl)-1,3-oxazinan-2-one was obtained from crystallization from ether/hexanes at −20° C. as a light yellow solid. $^1$H NMR (400 MHz, CDCl$_3$) 5.52 (br s, 1H), 4.38–4.33 (m, 1H), 4.28–4.22 (m, 1H), 3.70–3.59 (m, 2H), 3.46 (t, 1H), 1.97–1.93 (m, 1H), 1.72–1.67 (m, 1H), 0.91 (s, 9H), 0.90 (s, 6H).

Step 7

Preparation of isopropyl 7-[(4R)-4-(hydroxymethyl)-2-oxo-1,3-oxazinan-3-yl]heptanoate To a solution of (4R)-4-({[tert-butyl(dimethyl)silyl]oxy}methyl)-1,3-oxazinan-2-one (0.51 g, 2.078 mmol) in DMF (10 mL) at rt under N$_2$ was added KHMDS (0.5 M in toluene, 5 mL) dropwise (gel like precipitation formation) and the mixture was stirred for 10 min. Isopropyl 7-iodoheptanoate (1.24 g, 4.16 mmol, 2 eq) was then added in one portion and the mixture stirred at 65° C. for an additional 5 h and cooled to rt, diluted with water/ether. The layers were separated and the aqueous layer extracted with ether. The organic layers were combined, washed with water and brine, dried over MgSO$_4$ and filtered. The filtrate was concentrated in vacuo and the residue purified by column chromatography (15–30% acetone/toluene) to give desired product isopropyl 7-[(4R)-4-({[tert-butyl(dimethyl)silyl]oxy}methyl)-2-oxo-1,3-oxazinan-3-yl]heptanoate as a colorless oil. $^1$H NMR (400 MHz, Acetone-$d_6$): δ4.98–4.90 (1 H, m), 4.38–4.30 (1 H, m), 4.16–4.12 (1 H, m), 3.83–3.77 (2 H, m), 3.56–3.48 (2 H, m), 3.15–3.07 (1 H, m), 2.26 (2 H, t), 2.11–2.09 (2 H, m), 1.69–1.53 (4 H, m), 1.41–1.27 (4 H, m), 1.21 (6 H, d), 0.92 (9 H, s), 0.12 (6 H, s).

To the product thus obtained (0.6 g, 1.444 mmol) in THF (5 mL) was added AcOH (0.06 mL) and TBAF (1M in THF, 2.9 mL), and the mixture was stirred at rt for 30 min and then concentrated. The crude was purified by flash chromatography (30–50% acetone/toluene) to give desired product isopropyl 7-[(4R)-4-(hydroxymethyl)-2-oxo-1,3-oxazinan-3-yl]heptanoate. $^1$H NMR (400 MHz, Acetone-$d_6$):

δ 5.00–4.90 (1 H, m), 4.37–4.31 (1 H, m), 4.16–4.10 (2 H, m), 3.75–3.65 (2 H, m), 3.54–3.46 (2 H, m), 3.15–3.07 (1 H, m), 2.26 (2 H, t), 2.18–1.99 (2 H, m), 1.67–1.52 (4 H, m), 1.41–1.27 (4 H, m), 1.21 (6 H, d, J=6.2 Hz).

Step 8

Preparation of isopropyl 7-{(4R)-4-[(1E)-4,4-difluoro-3-oxo-4-phenylbut-1-en-1-yl]-2-oxo-1,3-oxazinan-3-yl}heptanoate A: oxidation of the alcohol: to a solution of DMSO (Dimethylsulfoxide) (113 uL, 1.592 mmol, 1.2 eq) in DCM (5 mL) at −78° C. was added Oxalyl chloride (128 uL, 1.46 mmol, 1.1 eq) dropwise and the mixture was stirred at the temperature for 15 min. Isopropyl 7-[(4R)-4-(hydroxymethyl)-2-oxo-1,3-oxazinan-3-yl]heptanoate (400 mg, 1.327 mmol) in DCM (3 mL) was added via a cannula and the mixture was stirred for an additional 15 min. Triethylamine (429 uL, 3.05 mmol, 2.3 eq) was then added in one portion and the mixture stirred at −78° C. for 30 min and allowed to warm to 0° C. slowly and concentrated in vacuo. The mixture was resuspended in ethyl acetate and filtered. The filtrate was concentrated in vacuo to give the crude aldehyde isopropyl 7-[(4R)-4-formyl-2-oxo-1,3-oxazinan-3-yl]heptanoate with good purity. $^1$H NMR (400 MHz, CDCl$_3$): δ 9.69 (1 H, d), 5.04–4.96 (1 H, m), 4.29–4.23 (1 H, m), 4.16–4.00 (2 H, m), 3.79–3.71 (1 H, m), 3.02–2.94 (1 H, m), 2.30–2.24 (4 H, m), 1.66–1.58 (4 H, m), 1.42–1.28 (4 H, m), 1.24 (6 H, d).

B: Preparation of the sodium salt of dimethyl (3,3-difluoro-2-oxo-3-phenylpropyl)phosphonate: to a solution of dimethyl (3,3-difluoro-2-oxo-3-phenylpropyl)phosphonate (5.24 g, 18.84 mmol) in ether (50 mL) at rt was added sodium hydride (60% oil dispersion, 791 mg, 19.78 mmol, 1.05 eq) portionwise and the white suspension was stirred at rt for 1 h. The mixture was filtered and the white solid washed with ether/hex. The solid thus obtained was dried under high vacuum to give white powder.

C: Horner-Emmons-Smith reaction: to a solution of isopropyl 7-[(4R)-4-formyl-2-oxo-1,3-oxazinan-3-yl]heptanoate (207 mg, 0.691 mmol) in THF (3 mL) was added Zinc chloride (0.5M in THF, 1.52 mL, 0.76 mmol, 1.1 eq) followed by the sodium salt of dimethyl (3,3-difluoro-2-oxo-3-phenylpropyl)phosphonate (270 mg, 0.898 mmol, 1.3 eq) as a solid and the mixture was heated to 60° C. o/n and concentrated. The residue was purified by column chromatography (80% ethyl acetate/hexanes) to give the desired product isopropyl 7-{(4R)-4-[(1E)-4,4-difluoro-3-oxo-4-phenylbut-1-en-1-yl]-2-oxo-1,3-oxazinan-3-yl}heptanoate as a light yellow oil. MS (+ESI): m/z 452 (M+1)$^+$.

Step 9

Compound 29: isopropyl 7-{(4R)-4-[(1E)-4,4-difluoro-3-hydroxy-4-phenylbut-1-en-1-yl]-2-oxo-1,3-oxazinan-3-yl}heptanoate To a solution of catecholborane (107 mg) in toluene (1 mL) was added (S)-2-methyl-CBS-oxaborolidine (1M in toluene, 0.89 mL) under N$_2$ at −78° C. and the mixture was stirred at the temperature for 1 h. Isopropyl 7-{(4R)-4-[(1E)-4,4-difluoro-3-oxo-4-phenylbut-1-en-1-yl]-2-oxo-1,3-oxazinan-3-yl}heptanoate (200 mg) in toluene (2 mL) was added via a cannula slowly and the mixture was stirred for an additional hour and quenched with 1N HCl. The mixture was allowed to warm to room temperature and extracted with DCM (2×). The organic layers were dried over Na$_2$SO$_4$ and filtered. The filtrate was concentrated in vacuo and the residue purified by column chromatography (80–100% ethyl acetate/hexanes) to give the title compound. MS (+ESI): m/z 454 (M+1)$^+$.

EXAMPLE 15

7-{(4R)-4-[(1E)-4,4-difluoro-3-hydroxy-4-phenyl-but-1-en-yl]-2-oxo-1,3-oxanzinan-3-yl}heptanoic acid MS (−ESI): m/z 410 (M−1)$^-$.

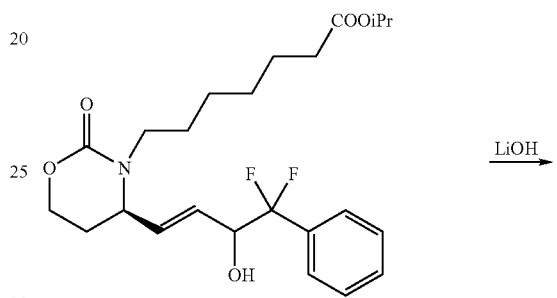

29

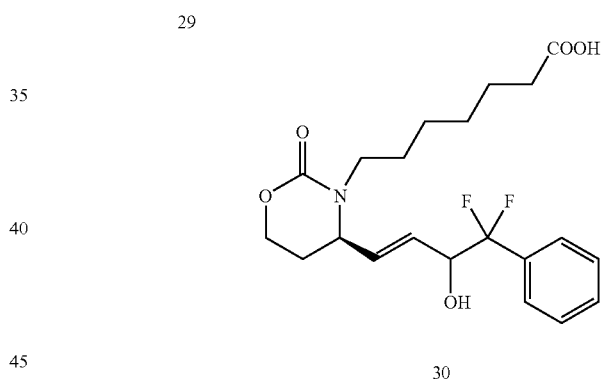

30

The isopropyl ester Compound 29 was first treated with a mixture of LiOH in Methanol/water followed by acidification with 1N HCl and extraction with ethyl acetate to give title compound. MS (−ESI): m/z 410 (M−1)$^-$.

I. Effects of an EP4 Agonist on Intraocular Pressure (IOP) in Rabbits and Monkeys.

Animals

Drug-naïve, male Dutch Belted rabbits and female cynomolgus monkeys are used in this study. Animal care and treatment in this investigation are in compliance with guidelines by the National Institute of Health (NIH) and the Association for Research in Vision and Ophthalmology (ARVO) resolution in the use of animals for research. All experimental procedures str approved by the Institutional Animal Care and Use Committee of Merck and Company.

Drug Preparation and Administration

Drug concentrations are expressed in terms of the active ingredient (base). The compounds of this invention are dissolved in physiological saline at 0.01, 0.001, 0.0001% for rabbit study and 0.05, 0.005% for monkey studies. Drug or vehicle aliquots (25 ul) are administered topically unilaterally or bilaterally. In unilateral applications, the contralateral eyes receive an equal volume of saline. Proparacaine (0.5%) is applied to the cornea prior to tonometry to minimize discomfort. Intraocular pressure (IOP) is recorded using a pneumatic tonometer (Alcon Applanation Pneumatonograph) or equivalent.

Analysis

The results are expressed as the changes in IOP from the basal level measured just prior to administration of drug or vehicle and represent the mean, plus or minus standard deviation. Statistical comparisons are made using the Student's t-test for non-paired data between responses of drug-treated and vehicle-treated animals and for paired data between ipsilateral and contralateral eyes at comparable time intervals. The significance of the date is also determined as the difference from the "t-0" value using Dunnett's "t" test. Asterisks represent a significance level of $p<0.05$.

A. Intraocular Pressure Measurement in Rabbits

Male Dutch Belted rabbits weighing 2.5–4.0 kg are maintained on a 12-hour light/dark cycle and rabbit chow. All experiments are performed at the same time of day to minimize variability related to diurnal rhythm. IOP is measured before treatment then the compounds of this invention or vehicle are instilled (one drop of 25 ul) into one or both eyes and IOP is measured at 30, 60, 120, 180, 240, 300, and 360 minutes after instillation. In some cases, equal number of animals treated bilaterally with vehicle only are evaluated and compared to drug treated animals as parallel controls.

B. Intraocular Pressure Measurements in Monkeys.

Unilateral ocular hypertension of the right eye is induced in female cynomolgus monkeys weighing between 2 and 3 kg by photocoagulation of the trabecular meshwork with an argon laser system (Coherent NOVUS 2000, Palo Alto, USA) using the method of Lee at al. (1985). The prolonged increase in intraocular pressure (IOP) results in changes to the optic nerve head that are similar to those found in glaucoma patients.

For IOP measurements, the monkeys are kept in a sitting position in restraint chairs for the duration of the experiment. Animals are lightly anesthetized by the intramuscular injection of ketamine hydrochloride (3–5 mg/kg) approximately five minutes before each IOP measurement and one drop of 0.5% proparacaine was instilled prior to recording IOP. IOP is measured using a pneumatic tonometer (Alcon Applanation Tonometer) or a Digilab pneumatonometer (Bio-Rad Ophthalmic Division, Cambridge, Mass., USA).

IOP is measured before treatment and generally at 30, 60, 124, 180, 300, and 360 minutes after treatment. Baseline values are also obtained at these time points generally two or three days prior to treatment. Treatment consists of instilling one drop of 25 ul of the compounds of this invention (0.05 and 0.005%) or vehicle (saline). At least one-week washout period is employed before testing on the same animal. The normotensive (contralateral to the hypertensive) eye is treated in an exactly similar manner to the hypertensive eye. IOP measurements for both eyes are compared to the corresponding baseline values at the same time point. Results are expressed as mean plus-or-minus standard deviation in mm Hg. The activity range of the compounds of this invention for ocular use is between 0.01 and 100,000 nM.

II. Radioligand Binding Assays:

The assays used to test these compounds were performed essentially as described in: Abramovitz M, Adam M, Boie Y, Carriere M, Denis D, Godbout C, Lamontagne S, Rochette C, Sawyer N, Tremblay N M, Belley M, Gallant M, Dufresne C, Gareau Y, Ruel R, Juteau H, Labelle M, Ouimet N, Metters K M. The utilization of recombinant prostanoid receptors to determine the affinities and selectivities of prostaglandins and related analogs. Biochim Biophys Acta 2000 Jan. 17;1483(2):285–293 and discussed below:

Stable Expression of Prostanoid Receptors in the Human Embryonic Kidney (HEK) 293(EBNA) Cell Line Prostanoid receptor (PG) cDNAs corresponding to full length coding sequences were subcloned into the appropriate sites of the mammalian expression vector pCEP4 (Invitrogen) pCEP4PG plasmid DNA was prepared using the Qiagen plasmid preparation kit (QIAGEN) and transfected into HEK 293(EBNA) cells using LipofectAMINE@ (GIBCO-BRL) according to the manufacturers' instructions. HEK 293(EBNA) cells expressing the cDNA together with the hygromycin resistance gene were selected in Dulbecco's Modified Eagle Medium (DMEM) supplemented with 10% heat inactivated fetal bovine serum, 1 mM sodium pyruvate, 100 U/ml Penicillin-G, 100 µg/ml Streptomycin sulphate, 250 µg/ml active GENETICIN™ (G418) (all from Life Technologies, Inc./BRL) and 200 µg/ml hygromycin (Calbiochem). Individual colonies were isolated after 2–3 weeks of growth under selection using the cloning ring method and subsequently expanded into clonal cell lines. Expression of the receptor cDNA was assessed by receptor binding assays.

HEK 293(EBNA) cells were grown in supplemented DMEM complete medium at 37° C. in a humidified atmosphere of 6% $CO_2$ in air, then harvested and membranes prepared by differential centrifugation (1000×g for 10 min, then 160,000×g for 30 min, all at 4° C.) following lysis of the cells by nitrogen cavitation at 800 psi for 30 min on ice in the presence of protease inhibitors (2 mM phenylmethylsulfonylfluoride, 10 µM E-64, 100 µM leupeptin and 0.05 mg/ml pepstatin). The 160,000×g pellets were resuspended in 10 mM HEPES/KOH (pH 7.4) containing 1 mM EDTA at approximately 5–10 mg/ml protein by Dounce homogenisation (Dounce A; 10 strokes), frozen in liquid nitrogen and stored at −80° C.

Prostanoid Receptor Binding Assays

Prostanoid receptor binding assays were performed in a final incubation volume of 0.2 ml in 10 mM MES/KOH (pH 6.0) (EP subtypes, FP and TP) or 10 mM HEPES/KOH (pH 7.4) (DP and IP), containing 1 mM EDTA, 10 mM $MgCl_2$ (EP subtypes) or 10 mM $MnCl_2$ (DP, FP, IP and TP) and radioligand [0.5–1.0 nM [$^3$H]$PGE_2$ (181 Ci/mmol) for EP subtypes, 0.7 nM [$^3$H]$PGD_2$ (115 Ci/mmol) for DP, 0.95 nM [$^3$H]$PGF_{2\alpha}$ (170 Ci/mmol) for FP, 5 nM [$^3$H]iloprost (16 Ci/mmol) for IP and 1.8 nM [$^3$H]SQ 29548 (46 Ci/mmol) for TP]. $EP_3$ assays also contained 100 µM GTPγS. The reaction was initiated by addition of membrane protein (approximately 30 µg for $EP_1$, 20 µg for $EP_2$, 2 µg for $EP_3$, 10 µg for $EP_4$, 60 µg for FP, 30 µg for DP, 10 µg for IP and 10 µg for TP) from the 160,000×g fraction. Ligands were added in dimethylsulfoxide ($Me_2SO$) which was kept constant at 1% (v/v) in all incubations. Non-specific binding was determined in the presence of 1 µM of the corresponding non-radioactive prostanoid. Incubations were conducted for 60 min (EP subtypes, FP and IP) or 30 min (DP and TP) at 30° C. (EP subtypes, DP, FP and TP) or room temperature (IP) and terminated by rapid filtration through a 96-well Unifilter GF/C (Canberra Packard) prewetted in assay incubation buffer without EDTA (at 4° C.) and using a Tomtec Mach III 96-well semi-automated cell harvester. The filters were washed with 3–4 ml of the same buffer, dried for 90 min at 55° C. and the residual radioactivity bound to the individual filters determined by scintillation counting with addition of 50 μl of Ultima Gold F (Canberra Packard) using a 1450 MicroBeta (Wallac). Specific binding was calculated by subtracting non-specific binding from total binding. Specific binding represented 90–95% of the total binding and was linear with respect to the concentrations of radioligand and protein used. Total binding represented 5–10% of the radioligand added to the incubation media.

The activity range of the compounds of this invention for bone use is between 0.01 and 100,000 nM.

Bone Resorption Assays:

1. Animal Procedures:

For mRNA localization experiments, 5-week old Sprague-Dawley rats (Charles River) are euthanized by $CO_2$, their tibiae and calvariae are excised, cleaned of soft tissues and frozen immediately in liquid nitrogen. For $EP_4$ regulation experiments, 6-week old rats are given a single injection of either vehicle (7% ethanol in sterile water) or an anabolic dose of $PGE_2$ (Cayman Chemical, Ann Arbor, Mich.), 3–6 mg/kg in the same vehicle) intraperitoneally. Animals are euthanized at several time points post-injection and their tibiae and calvariae, as well as samples from lung and kidney tissues are frozen in liquid nitrogen.

2. Cell Cultures

RP-1 periosteal cells are spontaneously immortalized from primary cultures of periosteal cells from tibae of 4-week old Sprague-Dawley rats and are cultured in DMEM (BRL, Gaithersburg, Md.) with 10% fetal bovine serum (JRH Biosciences, Lenexa, Kans.). These cells do not express osteoblastic phenotypic markers in early culture, but upon confluence, express type I collagen, alkaline phosphatase and osteocalcin and produce mineralized extracellular matrix.

RCT-1 and RCT-3 are clonal cell lines immortalized by SV-40 large T antigen from cells released from fetal rat calvair by a cmbination collagenase/hyaluronidase digestion. RCT-1 cells, derived from cells released during the first 10 minutes of digestion (fraction I), are cultured in RPMI 1640 medium (BRL) with 10% fetal bovine serum and 0.4 mg/ml G418 (BRL). These cells differentiate and express osteoblastic features upon retinoic acid treatment. RCT-3 cells, immortalized from osteoblast-enriched fraction III cells, are cultured in F-12 medium (BRL) with 5% Fetal bovine serum and 0.4 mg/ml G418. TRAB-11 cells are also immortalized by SV40 large T antigen from adult rat tibia and are cultured in RPMI 1640 medium with 10% FBS and 0.4 mg/ml G418. ROS 17/2.8 rat osteosarcoma cells are cultured in F-12 containing 5% FBS. Osteoblast-enriched (fraction i) primary fetal rat calvaria cells are obtained by collagenase/hyaluronidase digestion of calvariae of 19 day-old rat fetuses. See Rodan et al., *Growth stimulation of rat calvaria osteoblastic cells by acidic FGF, Endocrinology,* 121, 1919–1923 (1987), which is incorporated by reference herein in its entirety. Cells are released during 30–50 minutes digestion (fraction i) and are cultured in F-12 medium containing 5% FBS.

P815 (mouse mastocytoma) cells, cultured in Eagles MEM with 10% FBS, and NRK (normal rat kidney fibroblasts) cells, cultured in DMEM with 10% FBS, are used as positive and negative controls for the expression of $EP_4$, respectively. See Abramovitz et al., *Human prostanoid receptors: cloning and characterization*. In: Samuelsson B. et al. ed) *Advances in prostaglandin, Thrombosznes and leukotriene research*, vol. 23, pp. 499–504 (1995) and de Larco et al., *Epithelioid and fibroblastic rat kidney cell clones: EGF receptors and the effect of mouse sarcoma virus transformation, Cell Physiol.,* 94, 335–342 (1978), which are both incorporated by reference herein in their entirety.

3. Northern Blot Analysis:

Total RNA is extracted from the tibial metaphysis or diaphysis and calvaria using a guanidinium isothiocyanate-phenol-chloroform method after pulverizing frozen bone samples by a tissue homogenizer. See P. Chomczynski et al., *Single-step method of RNA isolation by acid guanidium thiocyanate-phenol-chloroform extraction., Analyt Biochem,* 162, 156–159 (1987), which is incorporated by reference herein in its entirety. RNA samples (20 mg) are separated on 0.9% agarose/formaldehyde gels and transferred onto nylon membranes (Boehringer Mannheim, Germany). Membranes are prehybridized in Hybrisol I (Oncor, Gaithersburg, Md.) and 0.5 mg/ml sonicated salmon sperm DNA (Boehringer) at 42° C. for 3 hours and are hybridized at 42° C. with rat $EP_2$ and mouse $EP_4$ cDNA probes labeled with $[^{32}P]dCTP$ (Amersham, Buckinghamshire, UK) by random priming using the rediprime kit (Amersham). After hybridization, membranes are washed 4 times in 2×SSC+ 0.1% SDS at room temperature for a total of 1 hour and once with 0.2×SSC+0.1% SDS at 55° C. for 1 hour and then exposed to Kodak XAR 2 film at −70° C. using intensifying screens. After developing the films, bound probes are removed twice with 0.1% SDS at 80° C. and membranes are hybridized with a human GAPDH (Glyceraldehyde 3-Phosphate Dehydrogenase) cDNA probe (purchased from Clontech, Palo Alto, Calif.) for loading control.

4. In-Situ Hybridization:

Frozen tibiae are sectioned coronally at 7 mm thickness and sections are mounted on charged slides (Probe On Plus, Fisher Scientific, Springfield, N.J.) and are kept at −70° C. until hybridization. cRNA probes are labeled with $^{35}S$-UTPgS (ICN, Costa Mesa, Calif.) using a Riboprobe II kit (Promega Madison, Wis.). Hybridization is performed overnight at 50° C. See M. Weinreb et al., *Different pattern of alkaline phosphatase, osteopontin and osteocalcin expression in developing rat bone visualized by in-situ hybridization, J. Bone Miner Res.,* 5, 831–842 (1990) and D. Shinar et al., *Expression of alphav and beta3 integrin subunits in rat osteoclasts in situ, J. Bone Miner. Res.,* 8, 403–414 (1993), which are both incorporated by reference herein in their entirety. Following hybridization and washing, sections are dipped in Ilford K5 emulsion diluted 2:1 with 6% glycerol in water at 42° C. and exposed in darkness at 4° C. for 12–14 days. Slides are developed in Kodak D-19 diluted 1:1 with water at 15°, fixed, washed in distilled water and mounted with glycerol-gelatin (Sigma) after hematoxylin staining. Stained sections are viewed under the microscope (Olympus, Hamburg, Germany), using either bright-field or dark-field optics.

5. Expression of $EP_4$ in Osteoblastic Cell Lines and in Bone Tissue.

The expression of $EP_4$ and $EP_2$ mRNA is examined in various bone derived cells including osteoblast-enriched primary rat calvaria cells, immortalized osteoblastic cell lines from fetal rat calvaria or from adult rat tibia and an osteoblastic osteosarcoma cell line. Most of the osteoblastic cells and cell lines show significant amounts of 3.8 kb $EP_4$ mRNA, except for the rat osteosarcoma cell line ROS 17/2.8. Consistent with this finding, in ROS 17/2.8 cells $PGE_2$ has no effect on intracellular cAMP, which is markedly induced in RCT-3 and TRAB-11 cells. Treatment of RCT-1 cells with retinoic acid, which promotes their differentiation, reduces the levels of $EP_4$ mRNA. NRK fibroblasts do not express $EP_4$ mRNA, while P815 mastocytoma cells, used as positive controls, express large amounts of $EP_4$ mRNA. In contrast to $EP_4$ mRNA, none of the osteoblastic cells and cell lines express detectable amounts of $EP_2$ mRA in total RNA samples. Expression of $EP_4$ mRNA in osteoblastic cells, $EP_4$ is also expressed in total RNA isolated from tibiae and calvariae of 5-week-old rats. In contrast, no $EP_2$ mRNA is found in RNA from tibial shafts.

6. $PGE_2$ Induces the Expression of $EP_4$ mRNA in RP-1 Periosteal Cells and in Adult Rat Tibiae $PGE_2$ enhances its own production via upregulation of cyclooxygenase 2 expression in osteoblasts and in bone tissue thus autoamplifying its own effects. $PGE_2$ also increases the levels of $EP_4$ mRNA. RP-1 cells are immortalized from a primary culture of adult rat tibia periosteum is examined. These cells express osteoblast phenotypic markers upon confluence and form mineralized bone matrix when implanted in nude mice. Similar to the other osteoblastic cells examined, RP-1 periosteal cells express a 3.8 kb $EP_4$ transcript. Treatment with $PGE_2$ ($10^{-6}$ M) rapidly increases $EP_4$ mRNA levels peaking at 2 hours after treatment. $PGE_2$ has no effect on $EP_4$ mRNA levels in the more differentiated RCT-3 cells pointing to cell-type specific regulation of $EP_4$ expression by $PGE_2$. $EP_2$ mRNA is not expressed in RP-1 cells before or after treatment with $PGE_2$.

To examine if $PGE_2$ regulates $EP_4$ mRNA levels in vivo in bone tissue, five-week-old male rats are injected with $PGE_2$ (3–6 mg/Kg). Systemic administration of $PGE_2$ rapidly increased $EP_4$ mRNA levels in the tibial diaphysis peaking at 2 h after injection. A similar effect of $PGE_2$ on $EP_4$ mRNA is observed in the tibial metaphysis and in calvaria. $PGE_2$ induces $EP_4$ mRNA levels in vitro in osteogenic periosteal cells and in vivo in bone tissue in a cell type-specific and tissue-specific manner. $PGE_2$ does not induce $EP_2$ mRNA in RP-1 cells nor in bone tissue.

7. Localization of $EP_4$ mRNA Expression in Bone Tissue

In situ hybridization is used in order to localize cells expressing $EP_4$ in bone. In control experiment (vehicle-injected) rats, low expression of $EP_4$ is detected in bone marrow cells. Administration of a single anabolic dose of $PGE_2$ increased the expression of $EP_4$ in bone marrow cells. The distribution of silver grains over the bone marrow is not uniform and occurs in clumps or patches in many areas of the metaphysis. Within the tibial metaphysis, $EP_4$ expression is restricted to the secondary spongiosa area and is not seen in the primary spongiosa. Hybridization of similar sections with a sense probe (negative control) does not show any signal.

$EP_4$ is expressed in osteoblastic cells in vitro and in bone marrow cells in vivo, and is upregulated by its ligand, $PGE_2$.

8. Agonists of the Present Invention

Using standard methods for measuring agonist activity, the following compounds are evaluated in cell cultures and in $EP_4$ receptor cell-free systems to determine the agonist activity of the compounds in terms of their $EC_{50}$ value.

What is claimed is:

1. A compound having the structural formula I:

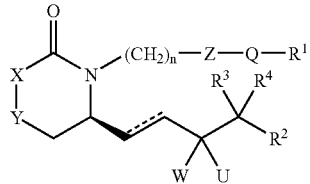

FORMULA I or a pharmaceutically acceptable salt, enantiomer, diastereomer, prodrug or mixture thereof, wherein, Q is $(CH_2)_m$, $(CH_2)_m C_{6-10}$aryl, $(CH_2)_m C_{5-10}$ heterocyclyl, $(CH_2)_m C_{3-10}$ heterocycloalkyl, $(CH_2)_m C_{3-8}$ cycloalkyl, $C(halo)_2$, said cycloalkyl, heterocycloalkyl, aryl or heterocyclyl unsubstituted or substituted with 1–3 groups of $R^a$;

X represents O,

Y represents $CH_2$;

U represents H, C1–3 alkyl or is not present when W is =O;

W represents OH or =O, provided that U is not present when W is =O;

$R^1$ represents $(CH_2)_p$hydroxy, $(CH_2)_p$CN, $(CH_2)_p CO_2 R^{10}$, $(CH_2)_n SO_3 R^6$, —$(CH_2)_p CF_2 SO_2 NH_2$, —$(CH_2)_p SO_2 NH_2$, —$(CH_2)_p CONHSO_2 R_2$, —$(CH_2)_p SO_2 NHCOR^2$, —$(CH_2)_p PO(OH)_2$, $(CH_2)_p CONHPO_2 R^6$, $(CH_2)_p CONHR^8$, $(CH_2)_p C_{1-4}$alkoxy, —$(CH_2)_p$cycloalkyl, or $(CH_2)_n$heterocyclyl, said heterocyclyl unsubstituted or substituted with 1 to 3 groups of $R^a$ and optionally containing an acidic hydroxyl group;

$R^2$ independently represents $C_{1-10}$ alkyl, $(CH_2)_m C_{6-10}$aryl, $(CH_2)_m C_{5-10}$heterocyclyl, $(CH_2)_m C_{3-10}$ heterocycloalkyl, $(CH_2)_m C_{3-8}$ cycloalkyl, O—$C_{1-10}$alkyl, O—$C_{6-10}$aryl, O—$C_{3-10}$cycloalkyl, O—$C_{3-10}$ heterocycloalkyl, O—$C_{3-10}$ heterocycloalkyl, said alkyl, cycloalkyl, heterocycloalkyl, aryl or hetrocyclyl unsubstituted or substituted with 1–3 groups of $R^a$;

$R^3$ and $R^4$ independently represents hydrogen, halogen, or $C_{1-6}$ alkyl, or $R^3$ and $R^4$ may be taken together to form a 3–7 membered carbon ring optionally interrupted with 1–2 heteroatoms chosen from O, S, SO, $SO_2$, and $NR^9$;

$R^6$ and $R^7$ independently represents hydrogen, or $C_{1-4}$ alkyl;

$R^8$ represents hydrogen, acyl, or sulfonyl;

$R^9$ represents hydrogen, $C_{1-6}$ alkyl, said alkyl optionally substituted with 1–3 halogen, CN, OH, $C_{1-6}$ alkoxy, $C_{1-6}$ acyloxy or amino;

$R^{10}$ represents hydrogen, $C_{1-10}$ alkyl, $C_{3-10}$ cyclcoalkyl, $(CH_2)_p C_{6-10}$ aryl, $(CH_2)_p C_{5-10}$ heterocyclyl, $CR^6 R^7 OC(O)O$ $C_{3-10}$ cycloalkyl or $CR^6 R^7 OC(O)O$ $C_{1-10}$ alkyl;

Z represents a C≡C, O, S, $(C(R^b)_2)_n$, or CH=CH;

$R^b$ represents hydrogen, $C_{1-6}$ alkyl or halogen;

$R^a$ represents $C_{1-6}$ alkoxy, $C_{1-6}$ alkyl, $CF_3$, nitro, amino, cyano, $C_{1-6}$ alkylamino, halogen, $SC_{1-6}$alkyl, $SC_{6-10}$ aryl, $SC_{5-10}$heterocyclyl, $CO_2 R^6$, $OC_{6-10}$aryl, $OC_{5-10}$ heterocyclyl, $CH_2 OC_{1-6}$ alkyl, $CH_2 SC_{1-6}$ alkyl, $CH_2 O$aryl, $CH_2 S$aryl;

----- represents a double or single bond;

p represents 0–3;

n represents 0–4; and m represents 0–8.

2. A compound in accordance with claim 1 wherein $R^1$ is $(CH_2)_p CN$, $(CH_2)_p CO_2 R^{10}$, —$(CH_2)_p PO(OH)_2$, $(CH_2)_p CONHPO_2 R^6$, $(CH_2)_p CONHR^8$, or $(CH_2)_n$heterocyclyl, said heterocyclyl unsubstituted or substituted with 1 to 3 groups of $R^a$ and all other variables are as originally described.

3. A compound in accordance with claim 2 wherein Z is a bond or S, Y is $CH_2$ and X is O, S or $CH_2$.

4. A compound in accordance with claim 1 wherein $R^1$ is $(CH_2)_p CO_2 R^{10}$, X is O, Y are $CH_2$, Z is $(C(R^b)_2)_n$, Q is $(CH_2)m$, $R^2$ is $(CH_2)_m C_{6-10}$aryl, said aryl unsubstituted or substituted with 1 to 3 groups of $R^a$.

5. A compound in accordance with claim 2 wherein $R^1$ is $(CH_2)_m C_{5-10}$heterocyclyl, U is H, or $C_{1-3}$ alkyl, W is OH, Z is a bond or S, $R^2$ is $(CH_2)_m C_{6-10}$aryl, said aryl unsubstituted or substituted with 1 to 3 groups of $R^a$, said heterocyclyl unsubstituted or substituted with 1 to 3 groups of $R^a$ and all other variables are as originally described.

6. A compound which is:
7-{(4S)-4-[(3R)-3-hydroxy-4-phenylbutyl]-2-oxo-1,3-oxazinan-3-yl}heptanoic acid;
5-(3-{(4R)-4-[(1E,3S)-3-hydroxy-4-phenylbut-1-enyl]-2-oxo-1,3-oxazinan-3-yl}propyl)thiophene-2-carboxylic acid;
isopropyl 5-(3-{(4R)-4-[(1E,3S)-3-hydroxy-4-phenylbut-1-enyl]-2-oxo-1,3-oxazinan-3-yl}propyl)thiophene-2-carboxylate;
or a pharmaceutically acceptable salt, enantiomer, diastereomer, prodrug or mixture thereof.

7. A pharmaceutical composition comprising a pharmaceutically acceptable carrier and a compound of formula I, as recited in claim 1.

8. A method for treating ocular hypertension or glaucoma comprising administration to a patient in need of such treatment a therapeutically effective amount of a compound of claim 1, said compound administered in a topical formulation as a solution or suspension.

9. A method for treating macular edema or macular degeneration, treating dry eye, increasing retinal and optic nerve head blood velocity, increasing retinal and optic nerve oxygen tension, comprising administration to a patient in need of such treatment a pharmaceutically effective amount of a compound of a compound as recited in claim 1.

10. The method according to claim 9 in which the topical formulation optionally contains xanthan gum or gellan gum.

* * * * *